(12) United States Patent
Deokar et al.

(10) Patent No.: US 9,907,796 B2
(45) Date of Patent: Mar. 6, 2018

(54) METHODS OF TREATING TUMORAL DISEASES, OR BACTERIAL OR VIRAL INFECTIONS

(71) Applicants: Rhushikesh Chandrabhan Deokar, Haryana (IN); Sundeep Dugar, San Jose, CA (US); Dinesh Mahajan, Haryana (IN); Milton Henry Werner, Marietta, GA (US)

(72) Inventors: Rhushikesh Chandrabhan Deokar, Haryana (IN); Sundeep Dugar, San Jose, CA (US); Dinesh Mahajan, Haryana (IN); Milton Henry Werner, Marietta, GA (US)

(73) Assignee: INHIBIKASE THERAPEUTICS, INC., Atlanta, GA (US)

( * ) Notice: Subject to any disclaimer, the term of this patent is extended or adjusted under 35 U.S.C. 154(b) by 0 days.

(21) Appl. No.: 15/266,802

(22) Filed: Sep. 15, 2016

(65) Prior Publication Data
US 2017/0000789 A1    Jan. 5, 2017

Related U.S. Application Data

(62) Division of application No. 14/046,682, filed on Oct. 4, 2013, now Pat. No. 9,487,500.

(60) Provisional application No. 61/709,704, filed on Oct. 4, 2012.

(51) Int. Cl.
| | | |
|---|---|---|
| A61K 31/506 | (2006.01) | |
| C07D 401/04 | (2006.01) | |
| A61K 45/06 | (2006.01) | |
| A61K 31/5377 | (2006.01) | |
| C07C 309/04 | (2006.01) | |
| A61K 31/095 | (2006.01) | |

(52) U.S. Cl.
CPC .......... *A61K 31/506* (2013.01); *A61K 31/095* (2013.01); *A61K 31/5377* (2013.01); *A61K 45/06* (2013.01); *C07C 309/04* (2013.01); *C07D 401/04* (2013.01)

(58) Field of Classification Search
CPC .................................................. C07D 401/14
See application file for complete search history.

(56) References Cited

U.S. PATENT DOCUMENTS

| | | | |
|---|---|---|---|
| 4,160,099 A | 7/1979 | Bodor | |
| 5,521,184 A | 5/1996 | Zimmermann | |
| 9,359,376 B2 * | 6/2016 | Dugar | C07D 401/14 |
| 2006/0275260 A1 * | 12/2006 | Riviere | A61K 31/506 |
| | | | 424/85.7 |
| 2014/0121367 A1 | 5/2014 | Dugar et al. | |

FOREIGN PATENT DOCUMENTS

| | | |
|---|---|---|
| WO | WO-02/42265 A2 | 5/2002 |
| WO | WO-0242276 A1 | 5/2002 |
| WO | WO-2005/072826 A2 | 8/2005 |
| WO | WO-2008/076265 A1 | 6/2008 |
| WO | WO-2011/081408 A2 | 7/2011 |
| WO | WO-2012/012750 A1 | 1/2012 |
| WO | WO-2012/127225 A1 | 9/2012 |
| WO | WO-2012/137225 A1 | 10/2012 |
| WO | WO-2014/054058 A2 | 4/2014 |

OTHER PUBLICATIONS

R. Capdeville et al., 1 Nature Reviews—Drug Discovery, 493-502 (2002).*
R.J. Napier et al., 10 Cell Host & Microbe, 475-478 (2011).*
J.H. Poupaert, Drug Design: Basic Principles and Applications, in 2 Encyclopedia of Pharmaceutical Technology 1362-1369, 1367 (James Swarbrick ed., 3rd ed., 2007).*
E. Kwong et al., 412 International Journal of Pharmaceutics, 1-7 (2011).*
B. Muller et al., Antiviral Strategies in, Antiviral Strategies 1-24, 4 (H.-G. Krausslich et al., eds., 2009).*
J.D. Henderer et al., Ocular Pharmacology, in Goodman & Gilman's The Pharmacological Basis of Therapeutics 1679-1737 (L. Burnton et al. eds., 11th ed., 2006).*
P.K. Buxton, ABC of Dermatology [e-book] (4th ed., BMJ Books, 2003).*
L.P. Fox et al., Dermatological Pharmacology, in Goodman & Gilman's The Pharmacological Basis of Therapeutics 1679-1705 (L. Burnton et al. eds., 11th ed., 2006).*
Y.S. Yoon et al., 9 The International Journal of Tuberculosis and Lung Disease, 1215-1219 (2005).*
Kinase Inhibitors, Methods in Molecular Biology 795 (B. Kuster ed., 2012).*
C.F. Waller "Imatinib mesylate." Small Molecules in Oncology 3-20 (Springer Berlin Heidelberg, 2010).*
J. Lennartsson et al., 3 Cancer Therapy, 5-28 (2005).*
P.M. Reeves, 11 Nature Medicine, 731-739 (2005).*
G. McFadden, 11 Nature Medicine, 711-712 (2005).*
Davidsen, et al., "N-(Acyloxyalkyl)pyridinium salts as soluble prodrugs of a potent platelet activating factor antagonist", J Med Chem, 37(26): 4423-4429 (1994).
Garcia, et al., "Productive Replication of Ebola Virus is Regulated by the c-Abl1 Tyrosine Kinase," Science Translational Medicine, 4(123): 1-10 (2012).
Koon, et al., "Phase II Trial of imatinib in AIDS-associated kaposi's sarcoma: AIDS malignancy consortium protocol 042," J Clin Oncol, 32(5): 402-408 (2014).
Newsome, et al., "Abl collaborates with Src family kinases to stimulate actin-based motility of vaccinia virus," Cellular Microbiology, 8(2): 233-241 (2006).
Reeves, et al., "Disabling poxvirus pathogenesis by inhibition of Abl-family tyrosine kinases," Nature Medicine, 11: 731-739 (2005).
Reeves, et al., "Variola and monkeypox viruses utilize conserved mechanisms of virion motility and release that depend on Abl and Src family tyrosine kinases," J Virol, 85(1): 21-31 (2011).

(Continued)

*Primary Examiner* — Alexander R Pagano
(74) *Attorney, Agent, or Firm* — David P. Halstead; Licas Watkins; Foley Hoag LLP

(57) ABSTRACT

Novel compounds and their synthesis are described. Methods for using these compounds in the prevention or treatment of cancer, a bacterial infection or a viral infection in a subject are also described.

20 Claims, No Drawings

(56) References Cited

OTHER PUBLICATIONS

Swimm, et al., "Abl family tyrosine kinases regulate sialylated ganglioside receptors for polyomavirus," J Virol, 84(9): 4243-4251 (2010).
Uebelhoer, et al., "High-throughput, luciferase-based reverse genetics systems for identifying inhibitors of Marburg and Ebola viruses," Antiviral Res, 106: 86-94 (2014).
"Kon-nichi-no Chiryoyaku," KK Nankodo, p. 181 (Feb. 15, 2003).
Wermuth et al., Saishin Soyaku-Kagaku, KK Technomic, pp. 271-281, 290-293 (Sep. 25, 1999).

* cited by examiner

METHODS OF TREATING TUMORAL DISEASES, OR BACTERIAL OR VIRAL INFECTIONS

CROSS-REFERENCE TO RELATED APPLICATIONS

The present application is a divisional of U.S. application Ser. No. 14/046,682, filed Oct. 4, 2013, which claims priority to and the benefit of U.S. Provisional Application Ser. No. 61/709,704, filed on Oct. 4, 2012, the entire contents of each of which are incorporated herein by reference.

STATEMENT REGARDING FEDERALLY SPONSORED RESEARCH OR DEVELOPMENT

This invention was made in part with Government support under Contract No. 1R43NS069213-01/343NS069213-01S1, awarded by the United States' National Institutes of Health. The Government has certain rights in this invention.

CREATE ACT STATEMENT

The inventions disclosed herein were made as a result of activities undertaken within the scope of a joint research agreement between Inhibikase Therapeutics, Inc. and Sphaera Pharma Pvt. Ltd., Haryana, India, which agreement was in effect on or before the invention of the claimed subject matter.

FIELD OF INVENTION

The present invention relates to novel compounds with improved pharmacokinetic and pharmacodynamic properties and a process for the synthesis of these compounds.

BACKGROUND OF INVENTION

Imatinib is the first of a new class of drugs that acts by specifically inhibiting a certain enzyme that is characteristic of a particular cancer cell, rather than non-specifically inhibiting and killing all rapidly dividing cells. Imatinib was a model for other targeted therapies that inhibited the class of enzymes, tyrosine kinases. Imatinib, present as its mesylate salt, multi-targets several pathways and is found to inhibit c-kit, PDGF-R and c-ABL. It is also known for its inhibition of T-cell proliferation stimulated by DCs and PHA. Imatinib Mesylate binds preferentially to ATP-binding sites of the c-kit proto-oncogene product, platelet-derived growth factor receptor (PDGF-R), and Abelson kinase (c-ABL) impeding the ensuing signal transduction. Imatinib, a reversible tyrosine kinase inhibitor, is effective in treatment of chronic myelogenous leukemia (CML), gastrointestinal stromal tumors, eosinophilic disorders, and systemic mast cell disease.

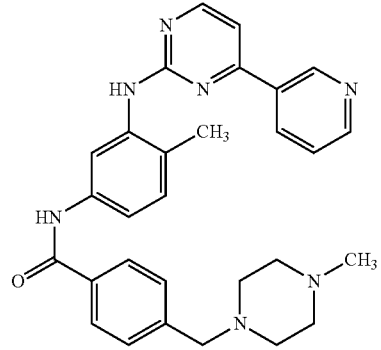

4-[(4-methylpiperazin-1-yl)methyl]-N-(4-methyl-3-{[4-(pyridin-3-yl)pyrimidin-2-yl]amino}phenyl)benzamide However, it is desirable to improve pharmacokinetic and if possible the pharmacodynamic parameters of imatinib, to favorably alter the dose and the dosing regimen of imatinib and to reduce the side effects.

SUMMARY OF INVENTION

The present invention comprises novel compounds that, when administered to a patient, provide an active form of imatinib.

The present application provides novel compounds of formula (I) or their pharmaceutically acceptable salts:

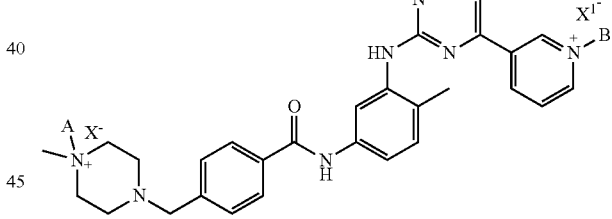

(I)

wherein:

A and B are independently selected from absent, H or a moiety of Formula (II), with the proviso that at least one of A and B is a moiety of Formula (II);

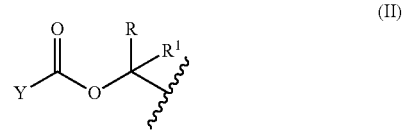

(II)

wherein:

R and $R^1$ are each independently selected from H, alkenyl, alkynyl, alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are optionally substituted with from 1 to 4 $C_1$-$C_8$ alkyl, alkoxy, aryl and heteroaryl substituents; or R and $R^1$ taken together with the atom to which they are attached form a 3- to 7-membered ring, wherein the 3- to 7-membered ring optionally contains up to two heteroatom groups selected from O, N $R^4$, S, SO and $SO_2$, and is optionally substituted with 1 to 4 alkoxy, F or Cl substituents;

Y is selected from $R^2$, $OR^2$, $NH_2$, $NHR^2$, and $NR^2R^3$;

$R^2$ is selected from alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl substituents;

$R^3$ is selected from alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl; or $R^2$ and $R^3$ may be taken together with the nitrogen atom to which they are attached to form a 3- to 7-membered ring, wherein the 3- to 7-membered ring optionally contains up to three heteroatom groups selected from O, $NR^4$, S, SO and $SO_2$, and is optionally substituted with alkoxy, F or Cl;

$R^4$ is, independently for each occurrence, selected from H or $C_1$-$C_8$ alkyl; and X and $X^1$ are each independently an anion or absent, provided that X is absent only when A is absent, and $X^1$ is absent only when B is absent.

The present application also provides a method for the preparation of novel compounds.

The present application also provides compositions comprising novel compounds.

The present application also provides for the use of the compounds for c-ABL, PDGFR and SCFR (c-Kit) inhibition.

DETAILED DESCRIPTION OF THE INVENTION

Accordingly, the present application provides novel compounds of formula (I) or their pharmaceutically acceptable salts and process for producing these compounds.

Compounds of the Present Invention

The present application provides novel compounds of formula (I) or their pharmaceutically acceptable salts:

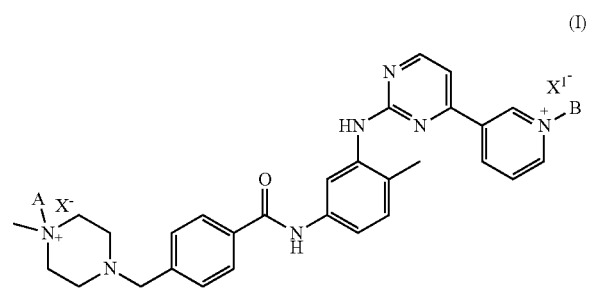

(I)

wherein:

A and B are independently selected from absent, H or a moiety of Formula (II), with the proviso that at least one of A and B is a moiety of Formula (II);

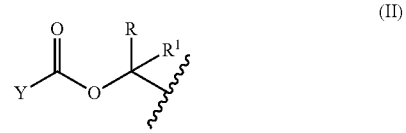

(II)

wherein:

R and $R^1$ are each independently selected from H, alkenyl, alkynyl, alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl and heteroaryl substituents; or R and $R^1$ taken together with the atom to which they are attached form a 3- to 7-membered ring, wherein the 3- to 7-membered ring optionally contains up to two heteroatom groups selected from O, $NR^4$, S, SO and $SO_2$, and is optionally substituted with 1 to 4 alkoxy, F or Cl substituents;

Y is selected from $R^2$, $OR^2$, $NH_2$, $NHR^2$, and $NR^2R^3$;

$R^2$ is selected from alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl substituents;

$R^3$ is selected from alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl; or $R^2$ and $R^3$ may be taken together with the nitrogen atom to which they are attached to form a 3- to 7-membered ring, wherein the 3- to 7-membered ring optionally contains up to three heteroatom groups selected from O, $NR^4$, S, SO and $SO_2$, and is optionally substituted with alkoxy, F or Cl;

$R^4$ is, independently for each occurrence, selected from H or $C_1$-$C_8$ alkyl; and X and $X^1$ are each independently an anion or absent, provided that X is absent only when A is absent, and $X^1$ is absent only when B is absent.

In some embodiments, R and $R^1$ are each independently selected from H and $C_1$-$C_8$ alkyl, such as H or methyl. Preferably both R and $R^1$ are H.

In some embodiments, $R^2$ and $R^3$ are independently selected from $C_1$-$C_8$ alkyl and aralkyl. In some such embodiments, $R^2$ and $R^3$ are independently selected from methyl, ethyl, isopropyl, tert-butyl, isobutyl, sec-butyl, 3-methylbut-2-yl, 1-phenylethyl, benzyl or cyclobutyl.

In some embodiments, $R^4$, independently for each occurrence, is selected from H and $C_1$-$C_8$ alkyl.

In some embodiments, X and $X^1$ are each independently halide or sulfonate, such as mesylate and iodide.

Because anions are not covalently attached to the molecule, it should be understood that X and $X^1$ are not necessarily located proximal to the atom bearing A or B, and should be viewed as interchangeable within any given molecule when both are present.

In some embodiments, A is H and B is a moiety of Formula (II).

In some embodiments, A is a moiety of Formula (II) and B is H.

In other embodiments, A is a moiety of Formula (II) and B is absent.

In yet other embodiments, A is absent and B is a moiety of Formula (II).

In certain embodiments, neither A nor B is

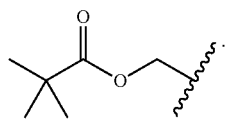 [SMILES: *COC(=O)C(C)(C)C]

Definitions

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Examplary alkenyl groups include allyl, propenyl, butenyl, 2-methyl-2-butenyl, and the like.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term alkoxy refers to an alkyl group singly bonded to oxygen.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, naphthyl, biphenyl, anthracenyl and the like.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The terms "cycloalkyl" and "cycloalkenyl" refer to cyclic hydrocarbon groups of 3 to 12 carbon atoms.

The terms "halogen", "halide" and "halo", as used herein, mean halogen and include fluoro, chloro, bromo and iodo.

The term "unsaturated ring" includes partially unsaturated and aromatic rings.

The terms "heterocyclyl", "heterocycle", "heterocyclo" and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The heterocyclic group may be attached at any heteroatom or carbon atom of the ring or ring system. Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like. Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo [2,3-c] pyridinyl, furo [3,2-b] pyridinyl] or furo [2,3-b] pyridinyl), dihydroisoindolyl, dihydroquinazolinyl (such as 3,4-dihydro-4-oxo-quinazolinyl), tetrahydroquinolinyl and the like. Exemplary tricyclic heterocyclic groups include carbazolyl, benzidolyl, phenanthrolinyl, acridinyl, phenanthridinyl, xanthenyl and the like.

The term "heteroalkyl", as used herein, refers to a saturated or unsaturated chain of carbon atoms including at least one heteroatom (e.g., O, S, or $NR^4$, such as where $R^4$ is H or lower alkyl).

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, quinolinyl, pyridazinyl, triazolyl, triazinyl, and the like.

The term "alkylene" in this text include both linear and branched, saturated and unsaturated (i.e. containing one double bond) divalent alkylene groups and monovalent alkyl groups, respectively.

The term "alkanol" in this text likewise includes linear and branched, saturated and unsaturated alkyl components of the alkanol groups, in which the hydroxyl groups may be situated at any position on the alkyl moiety. The term "cycloalkanol" includes unsubstituted or substituted (e.g. methyl or ethyl) cyclic alcohols.

The term "alkoxy" is intended to mean a alkyl radical, as defined herein, attached directly to an oxygen atom. Some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, 5-isobutoxy, sec-butoxy, and the like.

The term "heteroatom", as used herein, means an atom of any element other than carbon or hydrogen. Preferred heteroatoms are nitrogen, oxygen, and sulfur.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms.

As used herein, the term "tumoral disease" refers to a hyperproliferative disease, such as cancer.

As used herein, the term "conjoint administration" means administration of two or more agents to a subject of interest as part of a single therapeutic regimen. The administration(s) can be either simultaneous or sequential, i.e., administering one agent followed by administering of a second (and/or a third one, etc.) at a later time, as long as the agents administered co-exist in the subject being treated, or at least one agent will have the opportunity to act upon the same target tissues of other agents while said target tissues are still under the influence of said other agents. In a certain embodiment, agents to be administered can be included in a single pharmaceutical composition and administered together. In a certain embodiment, the agents are administered simultaneously, including through separate routes. In a certain embodiment, one or more agents are administered continuously, while other agents are administered only at predetermined intervals (such as a single large dosage, or twice a week at smaller dosages, etc.).

The present invention includes within its scope the salts and isomers. Compounds of the present invention may in some cases form salts which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxy ethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, wherein the substituent comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Solvates of the compounds of the invention are also contemplated herein. Solvates of the compounds of formula I are preferably hydrates or other pharmaceutically acceptable solvates.

All stereoisomers of the present compounds, such as those which may exist due to asymmetric carbons on the R substituents of the compound, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention may have the S or R configuration.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The present application also envisages within its scope the effect of selection of suitable counter ions. The counter ion of the compounds of the present invention may be chosen by selecting the dissociation constant for the drug capable of ionization within the said pH range. By estimating the ionized and un-ionized drug concentration of any compound (using well established equations such a Henderson-Hasselbach equation), the solubility and consequently the absorption of the drug may be altered.

The compounds of formula II may be divided in three classes i.e. Type I, where $Y=OR^2$; Type II, where $Y=R^2$ and Type III, where $Y=NR^2R^3$.

wherein $R^2$ and $R^3$ are as defined above

Non limiting Lists of Type I, Type II and type III reagents are presented below:

Type I Reagents
  i. chloromethyl isopropyl carbonate
  ii. benzyl chloromethyl carbonate
  iii. chloromethyl morpholinomethyl carbonate
  iv. chloromethyl isobutyl carbonate
  v. chloromethylmethyl carbonate
  vi. (S)-sec-butyl chloromethyl carbonate
  vii. (R)-sec-butyl chloromethyl carbonate
  viii. chloromethyl ((3S,5R)-3,5-dimethylmorpholino)methyl carbonate
  ix. chloromethyl 2-methylcyclopropyl carbonate
  x. chloromethyl2-methoxyethyl carbonate
  xi. chloromethyl propyl carbonate
  xii. chloromethyl cyclobutyl carbonate
  xiii. chloromethyl cyclopropyl carbonate
  xiv. chloromethyl 2,2-dimethylcyclobutyl carbonate
  xv. chloromethyl cyclopentyl carbonate
  xvi. chloromethyl oxetan-3-yl carbonate
  xvii. (S)-chloromethyl tetrahydrofuran-3-yl carbonate
  vviii. chloromethyl cyclohexylmethyl carbonate
  xix. chloromethyl 3-methoxycyclohexyl carbonate
  xx. (R)-chloromethyl tetrahydrofuran-3-yl carbonate
  xxi. chloromethyl ethoxymethyl carbonate
  xxii. chloromethyl oxepan-4-yl carbonate
  xxiii. (1R,2S,4S)-bicyclo[2.2.1]heptan-2-yl chloromethyl carbonate
  xxiv. chloromethyl 2,3-dihydro-1H-inden-1-yl carbonate
  xxv. benzyl chloromethyl carbonate
  xxvi. (S)-chloromethyl 1-phenylethyl carbonate
  xxvii. chloromethyl cyclohexyl carbonate
  xxviii. chloromethyl isobutyl carbonate
  xxix. chloromethyl 4-methylcyclohexyl carbonate
  xxx. chloromethyl 2-(methylthio)ethyl carbonate
  xxxi. chloromethyl 3-methylcyclohexyl carbonate
  xxxii. chloromethylpentan-2-yl carbonate
  xxxiii. chloromethyl neopentyl carbonate
  xxxiv. methyl 1-((chloromethoxy)carbonyloxy)cyclopropanecarboxylate
  xxxv. chloromethyl cyclopropylmethyl carbonate
  xxxvi. chloromethyl 2,2-diethoxyethyl carbonate
  xxxvii. chloromethyl cyclopentylmethyl carbonate
  xxxviii. methyl 2-((chloromethoxy)carbonyloxy)propanoate
  xxxix. (S)-chloromethyl 2,2,4-trimethylcyclopent-3-enyl carbonate
  xl. chloromethyl 1,3-dioxolan-2-yl carbonate
  xli. chloromethyl (2,6-dimethylcyclohexyl)methyl carbonate
  xlii. chloromethyl 2-(tetrahydro-2H-pyran-2-yl)ethyl carbonate
  xliii. chloromethyl(tetrahydro-2H-pyran-4-yl)methyl carbonate
  xliv. chloromethyl tetrahydro-2H-pyran-4-yl carbonate
  xlv. chloromethyl 1-methylcyclopentyl carbonate
  xlvi. chloromethyl 1-cyclopentylethyl carbonate
  xlvii. chloromethyl 3-methylcyclopentyl carbonate
  xlviii. chloromethyl 3,3-dimethylcyclohexyl carbonate
  xlix. chloromethyl 2,5-dimethylcyclohexyl carbonate
  l. chloromethyl 1-(4-methylcyclohexyl)ethyl carbonate
  li. chloromethyl (3-methyloxetan-3-yl)methyl carbonate
  lii. chloromethyl (3-methyloxetan-3-yl)methyl carbonate
  liii. chloromethyl 2-isopropoxyethyl carbonate
  liv. (chloromethyl carbonic) 5-((3aS,4S,6aR)-2-oxohexahydro-1H-thieno[3,4-d]imidazol-4-yl)pentanoic anhydride
  lv. 4-((chloromethoxy)carbonyloxy)-2-hydroxy-4-oxobutanoic acid
  lvi. chloromethyl 4-formyl-2-methoxyphenyl carbonate
  lvii. chloromethyl 3-oxobutan-2-yl carbonate
  lviii. methyl 4-((chloromethoxy)carbonyloxy)benzoate
  lix. (R)-2-amino-3-((chloromethoxy)carbonyloxy)propanoic acid
  lx. 3-tert-butyl-4-methoxyphenyl chloromethyl carbonate
  lxi. (R)-2-amino-3-(4-((chloromethoxy)carbonyloxy)phenyl)propanoic acid
  lxii. (R)-2-amino-4-((chloromethoxy)carbonyloxy)-4-oxobutanoic acid
  lxiii. (E)-chloromethyl 3,7-dimethylocta-2,6-dienyl carbonate
  lxiv. methyl 4-((chloromethoxy)carbonyloxy)benzoate
  lxv. chloromethyl 2-(4-methylcyclohex-3-enyl)propan-2-yl carbonate
  lxvi. chloromethyl 3,7-dimethylocta-1,6-dien-3-yl carbonate
  lxvii. 4-allyl-2-methoxyphenyl chloromethyl carbonate lxviii. chloromethyl (1R,2S,5R)-2-isopropyl-5-methylcyclohexyl carbonate
lxix. propyl 4-((chloromethoxy)carbonyloxy)benzoate
lxx. (E)-chloromethyl 3,7-dimethylocta-2,6-dienyl carbonate Type II Reagents
  i. chloromethyl cyclohexanecarboxylate
  ii. chloromethyl 2-cyclohexylacetate
  iii. chloromethyl 4-methylcyclohexanecarboxylate
  iv. chloromethyl 1-methylcyclohexanecarboxylate
  v. chloromethyl cyclopentanecarboxylate
  vi. chloromethyl 1-(trifluoromethyl)cyclopentanecarboxylate
  vii. chloromethyl cyclobutanecarboxylate
  viii. chloromethyl 2-ethylhexanoate
  ix. chloromethyl 3-cyclopentylpropanoate
  x. chloromethyl cyclopropanecarboxylate
  xi. chloromethyl pentanoate
  xii. chloromethyl 2-methylpentanoate
  xiii. chloromethyl 3,5,5-trimethylhexanoate
  xiv. chloromethyl 2,2-dimethylbutanoate
  xv. chloromethyl 2-methylbutanoate
  xvi. chloromethyl hexanoate
  xvii. chloromethyl 2-ethylbutanoate
  xviii. chloromethyl butyrate
  xix. chloromethyl 3-phenylpropanoate
  xx. chloromethyl 2-phenylpropanoate
  xxi. (R)-chloromethyl 2-phenylpropanoate
  xxii. (S)-chloromethyl 2-phenylpropanoate
  xxiii. (1r,4r)-chloromethyl 4-methylcyclohexanecarboxylate
  xxiv. chloromethyl 4-methoxycyclohexanecarboxylate
  xxv. chloromethyl 4,4-difluorocyclohexanecarboxylate
  xxvi. chloromethyl 3-methoxycyclohexanecarboxylate
  xxvii. (2R)-chloromethyl 2-methylcyclopentanecarboxylate
  xxviii. (R)-chloromethyl 2-methylbutanoate
  xxix. (S)-chloromethyl 2-methylbutanoate
  xxx. (S)-chloromethyl 2-methoxy-2-phenylacetate
  xxxi. (S)-chloromethyl 2-phenylpropanoate
  xxxii. (S)-chloromethyl 2-phenylbutanoate
  xxxiii. (S)-chloromethyl 3-phenylbutanoate
  xxxiv. bis(chloromethyl) 2,2-dimethylmalonate
  xxxv. bis(chloromethyl) oxalate
  xxxvi. chloromethyl 2-cyclopropylacetate
  xxxvii. chloromethyl 2-cyclobutylacetate
  xxxviii. chloromethyl 2-cyclopentylacetate
  xxxix. chloromethyl 2-(tetrahydrofuran-3-yl)acetate
  xl. chloromethyl 2-(tetrahydro-2H-pyran-4-yl)acetate
  xli. chloromethyl 2-methylcyclopropanecarboxylate
  xlii. chloromethyl 2-(1-methylcyclobutyl)acetate
  xliii. chloromethyl 2-(1-methylcyclopropyl)'acetate
  xliv. chloromethyl propionate
  xlv. chloromethyl acetate
  xlvi. chloromethyl isobutyrate
  xlvii. chloromethyl 2-isopropyl-3-methylbutanoate
  xlviii. chloromethyl 3,5-dimethylcyclohexanecarboxylate
  xlix. chloromethyl 2-propylpentanoate
  l. chloromethyl 4-methoxybenzoate
  li. chloromethyl 4-methylbenzoate
  lii. chloromethyl 3-methylbenzoate
  liii. chloromethyl 2,2,2-trifluoroacetate
  liv. chloromethyl 5,5-dimethyl-3-oxohexanoate
  lv. bis(chloromethyl) cyclopropane-1,1-dicarboxylate
  lvi. chloromethyl 1,2-dihydrocyclobutabenzene-1-carboxylate
  lvii. chloromethyl 2-cyclopentenylacetate
  lviii. chloromethyl 2-phenylbutanoate
  lix. chloromethyl 2,2-difluoroacetate
  lx. chloromethyl 4-fluorobenzoate
  lxi. chloromethyl 3-cyclohexylpropanoate
  lxii. chloromethyl 2-cyclohexylacetate
  lxiii. chloromethyl 3-(tetrahydro-2H-pyran-4-yl)propanoate
  lxiv. chloromethyl 2-(tetrahydro-2H-pyran-3-yl)acetate
  lxv. chloromethyl 3-(tetrahydro-2H-pyran-3-yl)propanoate
  lxvi. chloromethyl nicotinate Type III Reagents
  i. chloromethyl isopropylcarbamate
  ii. chloromethyl diisopropylcarbamate
  iii. chloromethyl dimethylcarbamate
  iv. chloromethyl isobutylcarbamate
  v. chloromethyl methylcarbamate
  vi. chloromethyl ethyl(isopropyl)carbamate
  vii. chloromethylisobutyl(methyl)carbamate
  viii. (S)-chloromethyl sec-butylcarbamate
  ix. chloromethyl methylcarbamate
  x. chloromethyl isopropyl(methyl)carbamate
  xi. chloromethyl propylcarbamate
  xii. chloromethyl 2-methoxyethylcarbamate
  xiii. chloromethyl methyl(propyl)carbamate
  xiv. chloromethyl diisobutylcarbamate
  xv. chloromethyl tert-butyl(isopropyl)carbamate
  xvi. chloromethyl di-sec-butylcarbamate
  xvii. chloromethyl aziridine-1-carboxylate
  xviii. chloromethyl 2-methylcyclopropylcarbamate
  xix. chloromethyl cyclopropylcarbamate
  xx. chloromethyl cyclopropylmethyl(propyl)carbamate
  xxi. chloromethyl cyclopropyl(methyl)carbamate
  xxii. chloromethyl azetidine-1-carboxylate
  xxiii. chloromethyl cyclobutylcarbamate
  xxiv. chloromethyl 2,2-dimethylcyclobutylcarbamate
  xxv. chloromethyl 3-methoxyazetidine-1-carboxylate
  xxvi. chloromethyl cyclobutyl(methyl)carbamate
  xxvii. chloromethyl oxetan-3-ylcarbamate
  xxviii. (S)-chloromethyl 2-methylpyrrolidine-1-carboxylate
  xxix. chloromethyl cyclopentylcarbamate
  xxx. chlorometh1 cyclopentyl(methyl)carbamate
  xxxi. chloromethyl tetrahydrofuran-3-ylcarbamate
  xxxii. chloromethyl piperidine-1-carboxylate
  xxxiii. (2R,6S)-chloromethyl 2,6-dimethylpiperidine-1-carboxylate
  xxxiv. (R)-chloromethyl 2-methylpiperidine-1-carboxylate
  xxxv. chloromethyl piperidine-1-carboxylate
  xxxvi. chloromethyl 3-methoxycyclohexylcarbamate
  xxxvii. chloromethyl cyclohexylmethylcarbamate
  xxxviii. chloromethyl cyclohexylmethyl(methyl)carbamate
  xxxix. chloromethyl morpholine-4-carboxylate
  xl. (3S,5R)-chloromethyl 3,5-dimethylmorpholine-4-carboxylate
  xli. (3R,5S)-chloromethyl 3,5-dimethylmorpholine-4-carboxylate
  xlii. (2S,6R)-chloromethyl 2,6-dimethylmorpholine-4-carboxylate
  xliii. chloromethyl 4-methylpiperazine-1-carboxylate
  xliv. chloromethylazepane-1-carboxylate
  xlv. chloromethylcycloheptylcarbamate
  xlvi. chloromethyl oxepan-4-ylcarbamate
  xlvii. chloromethyl (1R,2S,4S)-bicyclo[2.2.1]heptan-2-ylcarbamate xlviii. chloromethyl 2,3-dihydro-1H-inden-1-ylcarbamate
xlix. chloromethyl benzylcarbamate
l. (S)-chloromethyl 1-phenylethylcarbamate
li. ethyl 2-((chloromethoxy)carbonylamino)-3-methylbutanoate
lii. ethyl 2-((chloromethoxy)carbonylamino)-3-phenylpropanoate
liii. (S)-diethyl 2-((chloromethoxy)carbonylamino)pentanedioate
liv. ethyl((chloromethoxy)carbonylamino)propanoate
lv. ethyl 2-amino-6-((chloromethoxy)carbonylamino)hexanoate
lvi. ethyl 2-((chloromethoxy)carbonylamino)-4-methylpentanoate
lvii. ethyl 2-((chloromethoxy)carbonylamino)-3-methylpentanoate
lviii. (S)-dimethyl 2-((chloromethoxy)carbonylamino)succinate
lix. (S)-ethyl 2-((chloromethoxy)carbonylamino)-5-guanidinopentanoate
lx. (S)-ethyl 4-amino-2-((chloromethoxy)carbonylamino)-4-oxobutanoate
lxi. (S)-ethyl 2-amino-5-((chloromethoxy)carbonylamino)pentanoate
lxii. (S)-ethyl 5-amino-2-((chloromethoxy)carbonylamino)-5-oxopentanoate
lxiii. ethyl 2-((chloromethoxy)carbonylamino)-4-(methylthio)butanoate
lxiv. 1-chloromethyl 3-methyl 2-methyl-5,6-dihydropyridine-1,3(2H)-dicarboxylate
lxv. (S)-chloromethyl (1-methylpyrrolidin-2-yl)methyl carbonate
lxvi. (R)-chloromethyl (1-methylpyrrolidin-2-yl)methyl carbonate
lxvii. (S)-(1-benzylpyrrolidin-2-yl)methyl chloromethyl carbonate
lxviii. chloromethyl 1H-pyrrole-1-carboxylate
lxix. chloromethyl 2-nicotinoylhydrazinecarboxylate
lxx. (6S)-3-chloro-7-((chloromethoxy)carbonylamino)-8-oxo-5-thia-1-azabicyclo[4.2.0]oct-2-ene-2-carboxylic acid
lxxi. (6S)-7-((chloromethoxy)carbonylamino)-8-oxo-3-vinyl-5-thia-1-azabicyclo[4.2.0]oct-2-ene-2-carboxylic acid
lxxii. (6S)-7-((chloromethoxy)carbonylamino)-3-(methoxymethyl)-8-oxo-5-thia-1-azabicyclo[4.2.0]oct-2-ene-2-carboxylic acid
lxxiii. (6R,7R)-7-((chloromethoxy)carbonylamino)-3-methoxy-8-oxo-5-thia-1-azabicyclo[4.2.0]oct-2-ene-2-carboxylic acid
lxxiv. chloromethyl 3-(4-chlorophenyl)-1H-pyrazole-1-carboxylate
lxxv. chloromethyl 3-(4-fluorophenyl)-1H-pyrazole-1-carboxylate
lxxvi. chloromethyl 3-phenyl-1H-pyrazole-1-carboxylate
lxxvii. chloromethyl 3-(4bromophenyl)-1H-pyrazole-1-carboxylate
lxxviii. chloromethyl 2-cyano-1H-pyrrole-1-carboxylate
lxxix. chloromethyl 4-oxopiperidine-1-carboxylate
lxxx. 1-chloromethyl 3-ethyl 2-oxopiperidine-1,3-dicarboxylate
lxxxi. chloromethyl 2,2,6,6-tetramethyl-4-oxopiperidine-1-carboxylate
lxxxii. chloromethyl 2-oxopiperidine-1-carboxylate The novel compounds of the present application include compounds of Formula (III) and Formula (IV):

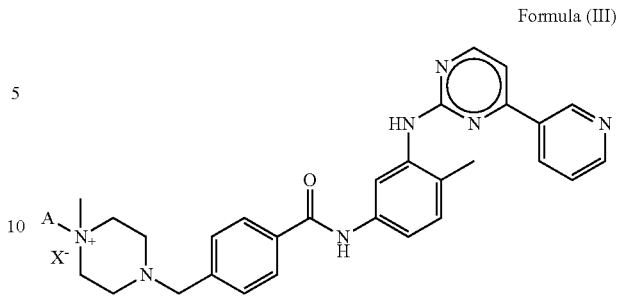

Formula (III)

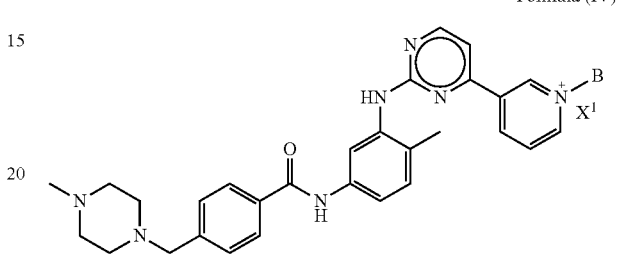

Formula (IV)

Where A or B=

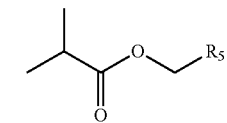

101

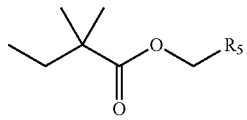

102

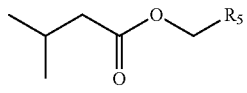

103

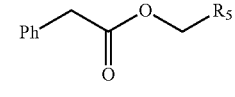

104

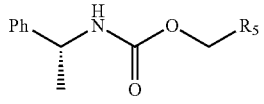

105

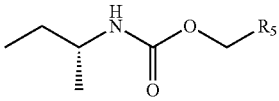

106

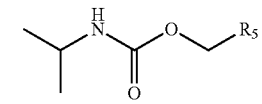

107

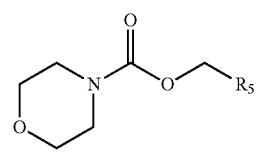

108

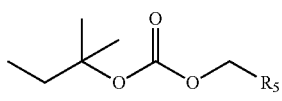 109

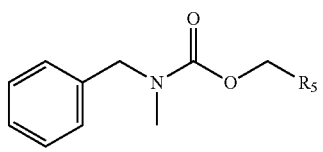 117

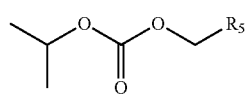 110

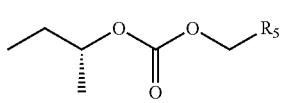 111

 118

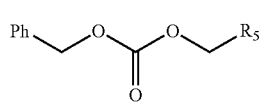 112

 119

 120

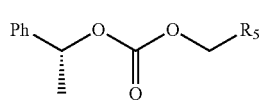 113

 121

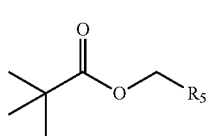 114 where $R^5$ represents a nitrogen atom of the imatinib moiety linked to A or B, and X may be iodide, chloride, bromide, mesylate, tosylate, or any other pharmaceutically acceptable anion to provide a pharmaceutically acceptable salt.

The compounds generated may be present as a single stereoisomer (e.g., enriched to at least 95% purity relative to the total amount of all stereoisomers present), a racemate, or a mixture of enantiomers or diastereomers in any ratio.

The novel compounds herein may be any of the compounds as below:

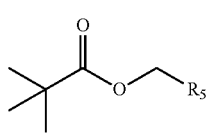 115

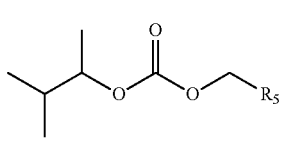 116

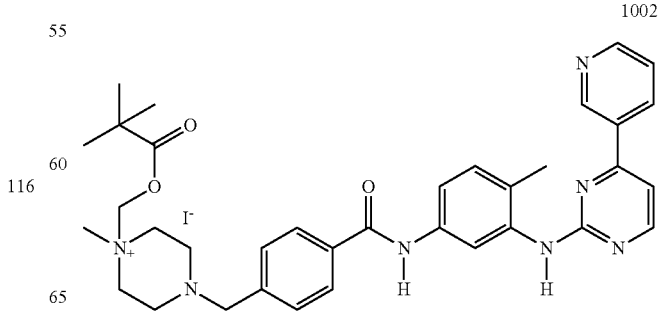 1002

17

1-methyl-4-(4-((4-methyl-3-((4-(pyridin-3-yl)pyrimidin-2-yl)amino)phenyl)carbamoyl)benzyl)-1-((pivaloyloxy)methyl)piperazin-1-ium iodide

18

1-methyl-4-(4-((4-methyl-3-((4-(pyridin-3-yl)pyrimidin-2-yl)amino)phenyl)carbamoyl)benzyl)-1-(((morpholine-4-carbonyl)oxy)methyl)piperazin-1-ium iodide

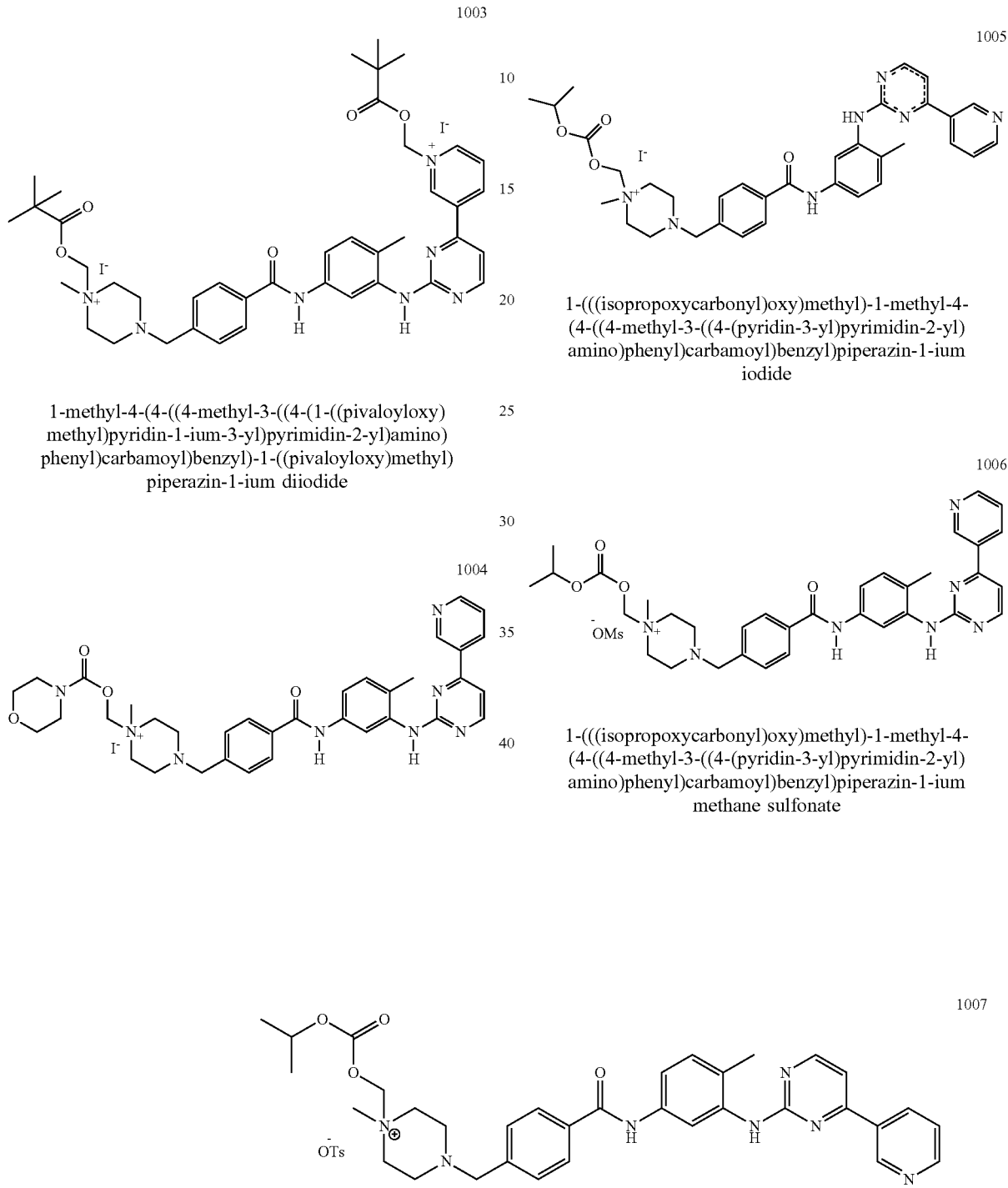

1-methyl-4-(4-((4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium diiodide 1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide 1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium methane sulfonate 1-(((isopropoxycarbonyl)oxy)methyl)-1-methyl-4-
(4-((4-methyl-3-((4-(pyridin-3-yl)pyrimidin-2-yl)
amino)phenyl)carbamoyl)benzyl)piperazin-1-ium
p-tolyl sulfonate

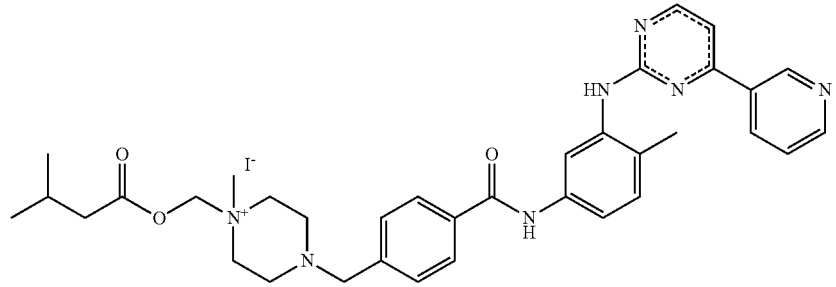

1008

1-methyl-4-(4-(4-methyl-3-(4-(pyridin-3-yl)pyrimi-
din-2-ylamino)phenylcarbamoyl)benzyl)-1((3-meth-
ylbutanoyloxy)methyl)piperazin-1-ium iodide

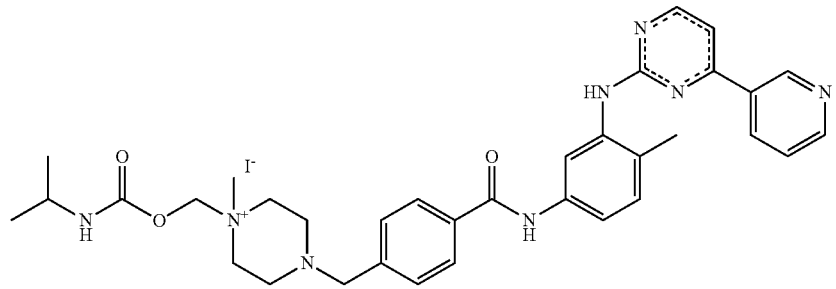

1009

1-((isopropylcarbamoyloxy)methyl)-1-methyl-4-(4-
(4-methyl-3-(4-(pyridin-3-yl)pyrimidin-2-ylamino)
phenylcarbamoyl)benzyl)piperazin-1-ium iodide

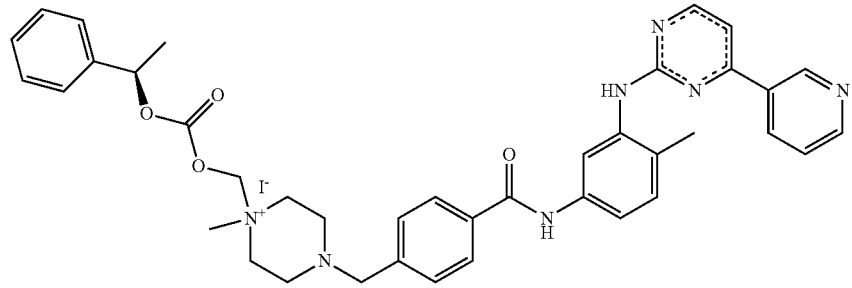

1010

(R)-1-methyl-4-(4-(4-methyl-3-(4-(pyridin-3-yl)
pyrimidin-2-ylamino)phenylcarbamoyl)benzyl)-1-
(((1-phenylethoxy)carbonyloxy)methyl)piperazin-1-
ium iodide

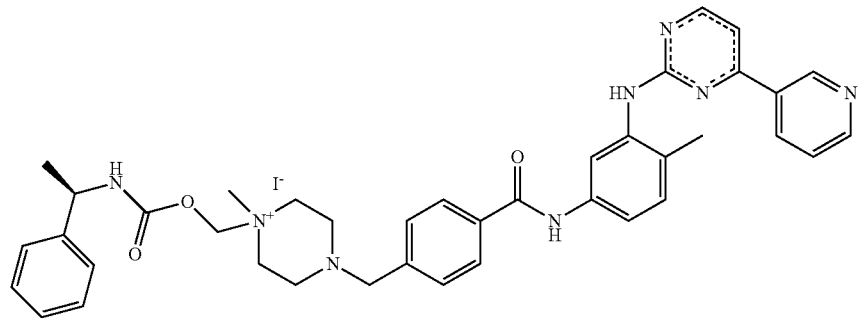

(R)-1-methyl-4-(4-(4-methyl-3-(4-(pyridin-3-yl)
pyrimidin-2-ylamino)phenylcarbamoyl)benzyl)-1-
((1-phenylethylcarbamoyloxy)methyl)piperazin-1-
ium iodide

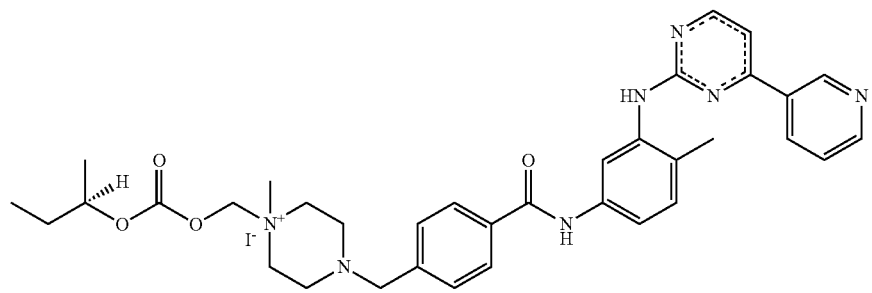

(R)-1-((sec-butoxycarbonyloxy)methyl)-1-methyl-4-
(4-(4-methyl-3-(4-(pyridin-3-yl)pyrimidin-2-
ylamino)phenylcarbamoyl)benzyl)piperazin-1-ium
iodide

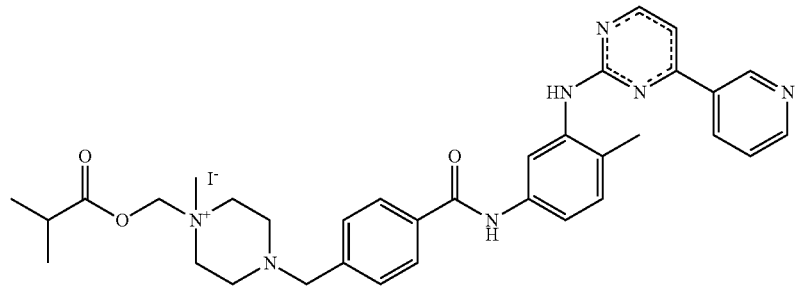

1-(isobutyryloxymethyl)-1-methyl-4-(4-(4-methyl-3-(4-(pyridin-3-yl)pyrimidin-2-ylamino)phenylcarbamoyl)benzyl)piperazin-1-ium iodide

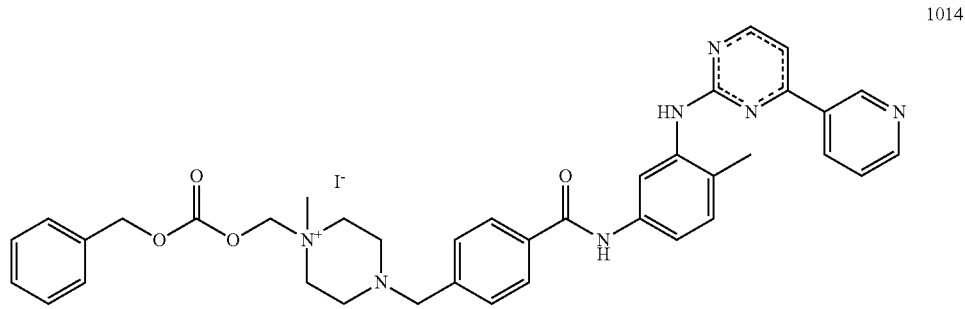

1-((benzyloxycarbonyloxy)methyl)-1-methyl-4-(4-(4-methyl-3-(4-(pyridin-3-yl)pyrimidin-2-ylamino)phenylcarbamoyl)benzyl)piperazin-1-ium iodide

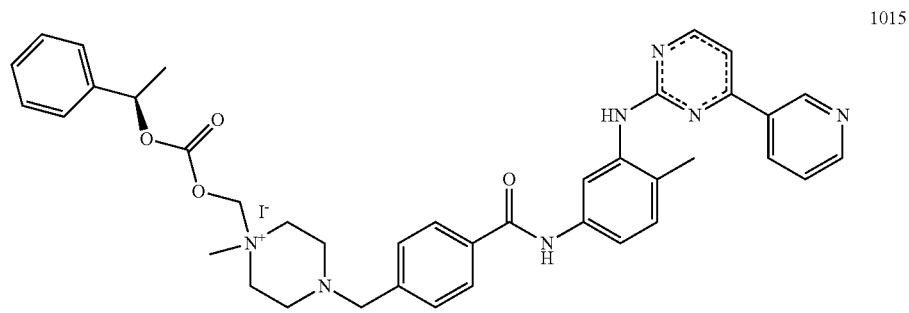

(R)-1-methyl-4-(4-(4-methyl-3-(4-(pyridin-3-yl)pyrimidin-2-ylamino)phenylcarbamoyl)benzyl)-1-(((1-phenylethoxy)carbonyloxy)methyl)piperazin-1-ium iodide

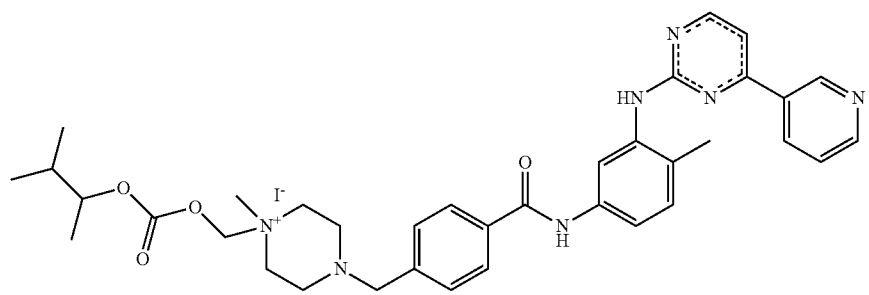

1-methyl-4-(4-(4-methyl-3-(4-(pyridin-3-yl)pyrimidin-2-ylamino)phenylcarbamoyl)benzyl)-1-(((3-methylbutan-2-yloxy)carbonyloxy)methyl)piperazin-1-ium iodide

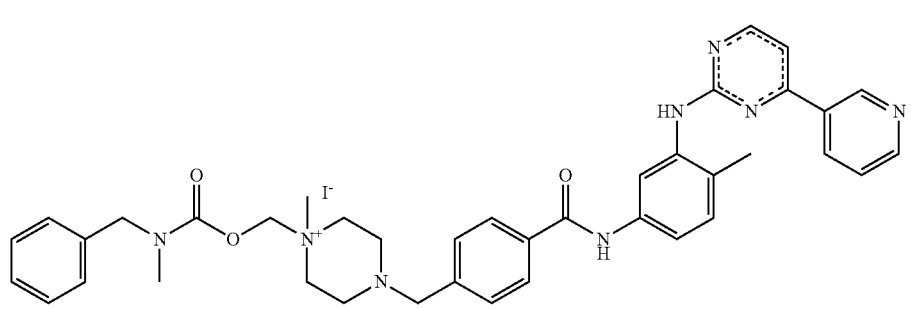

1-((benzyl(methyl)carbamoyloxy)methyl)-1-methyl-4-(4-(4-methyl-3-(4-(pyridin-3-yl)pyrimidin-2-ylamino)phenylcarbamoyl)benzyl)piperazin-1-ium iodide

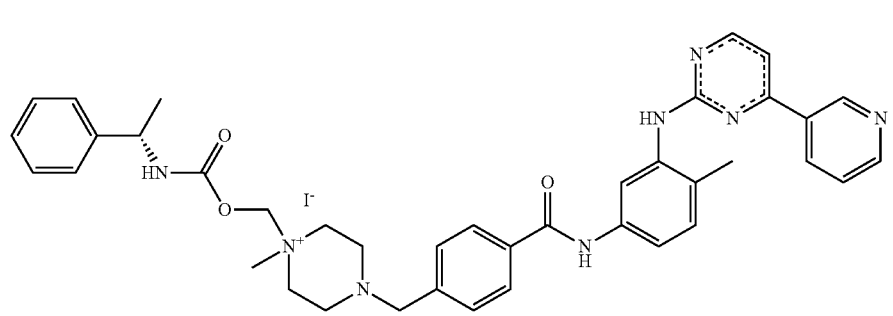

(S)-1-methyl-4-(4-(4-methyl-3-(4-(pyridin-3-yl)pyrimidin-2-ylamino)phenylcarbamoyl)benzyl)-1-((1-phenylethylcarbamoyloxy)methyl)piperazin-1-ium iodide

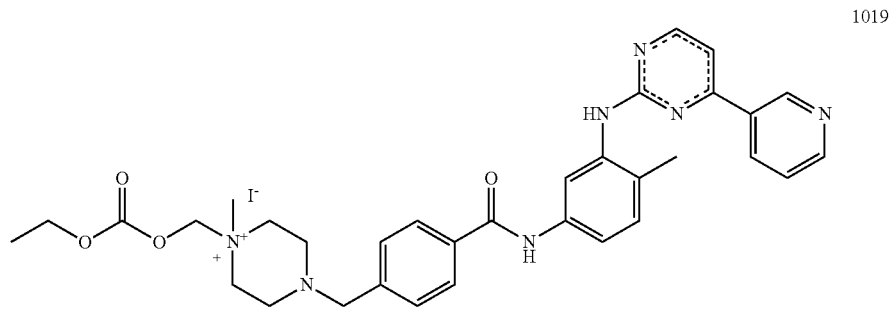

1-((ethoxycarbonyloxy)methyl)-1-methyl-4-(4-(4-methyl-3-(4-(pyridin-3-yl)pyrimidin-2-ylamino)phenylcarbamoyl)benzyl)piperazin-1-ium iodide

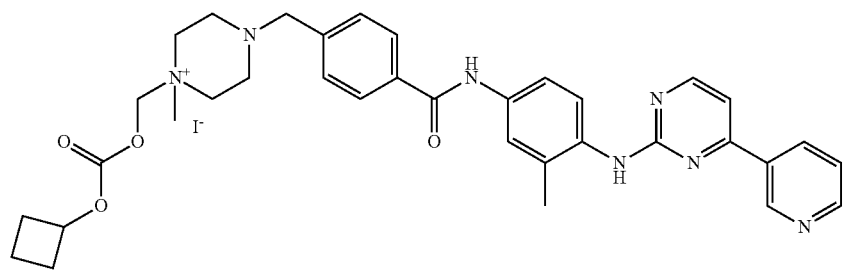
1020

1-((cyclobutoxycarbonyloxy)methyl)-1-methyl-4-(4-(3-methyl-4-(pyridin-3-yl)pyrimidin-2-ylamino)phenylcarbamoyl)benzyl)piperazin-1-ium iodide

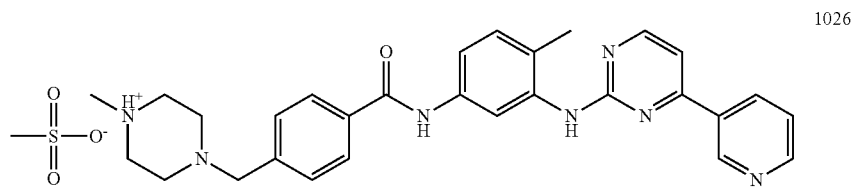
1026

1-methyl-4-(4-((4-methyl-3-((4-(pyridin-3-yl)pyrimidin-2-yl)amino)phenyl)carbamoyl)benzyl)piperazin-1-ium methanesulfonate 1027
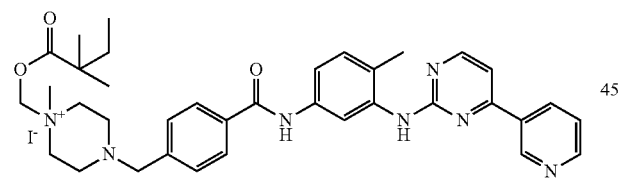

1-2,2-dimethylbutanoyloxy)methyl)-1-methyl-4-(4-(4-methyl-3-(4-(pyridin-3-yl)pyrimidin-2-ylamino)phenylcarbamoyl)benzyl)piperazin-1-ium iodide 1028
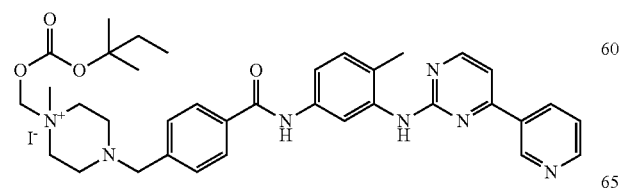

29

1-methyl-4-(4-(4-methyl-3-(4-(pyridin-3-yl)pyrimidin-2-ylamino)phenylcarbamoyl)benzyl)-1-((tert-pentyloxycarbonyloxy)methyl)piperazin-1-ium iodide

30

4-(4-((3-((4-(1-(((isopropoxycarbonyl)oxy)methyl)pyridin-1-ium-3-yl)pyrimidin-2-yl)amino)-4-methyl-phenyl)carbamoyl)benzyl)-1-methylpiperazin-1-ium

1029

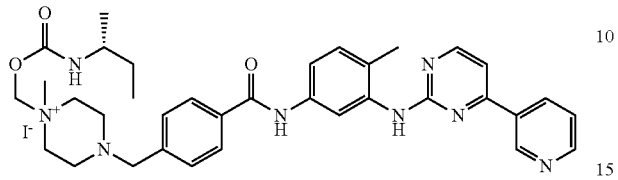

(R)-1-((sec-butylcarbamoyloxy)methyl)-1-methyl-4-(4-(4-methyl-3-(4-(pyridin-3-yl)pyrimidin-2-ylamino)phenylcarbamoyl)benzyl)piperazin-1-ium iodide 4-(4-((3-((4-(1-(((isopropoxycarbonyl)oxy)methyl)pyridin-1-ium-3-yl)pyrimidin-2-yl)amino)-4-methyl-phenyl)carbamoyl)benzyl)-1-methylpiperazin-1-ium monoiodide monomesylate

1030

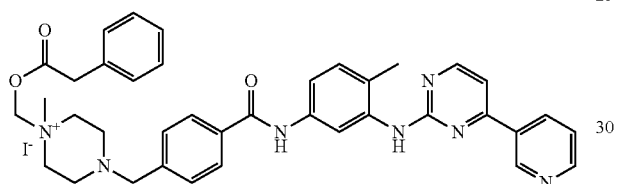

1-methyl-4-(4-(4-methyl-3-(4-(pyridin-3-yl)pyrimidin-2-ylamino)phenylcarbamoyl)benzyl)-1-((2-phenylacetoxy)methyl)piperazin-1-ium iodide

1032

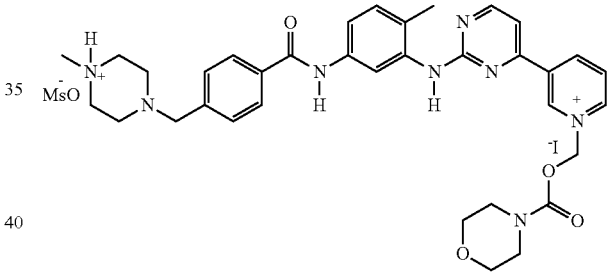

1031

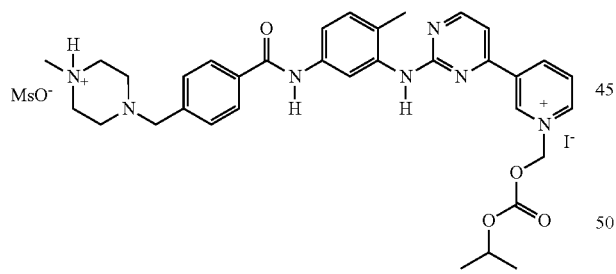

3-(2-((2-methyl-5-(4-((4-methylpiperazin-1-yl)methyl) benzamido)phenyl)amino)pyrimidin-4-yl)-1-(((morpholine-4-carbonyl)oxy)methyl)pyridin-1-ium monoiodide monomesylate

TABLE 1

| No. | Structure | IUPAC name | m/z |
|---|---|---|---|
| 1030 | 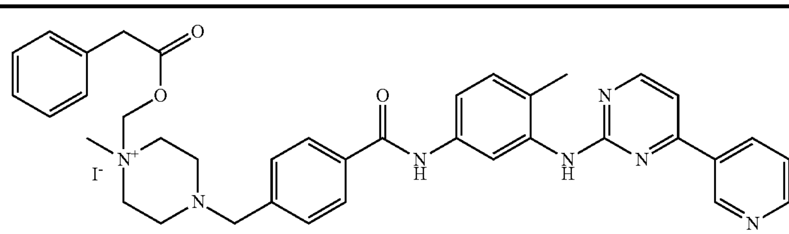 | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium iodide | 643 |

TABLE 1-continued

| No. | Structure | IUPAC name | m/z |
|---|---|---|---|
| 10737.02 | 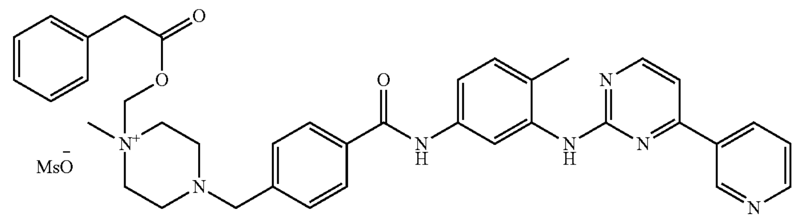 [SMILES: "MsO" ; Cc1ccc(NC(=O)c2ccc(CN3CC[N+](C)(COC(=O)Cc4ccccc4)CC3)cc2)cc1Nc1nccc(-c2cccnc2)n1] | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium methanesulfonate | 643 |
| 10737.04 | 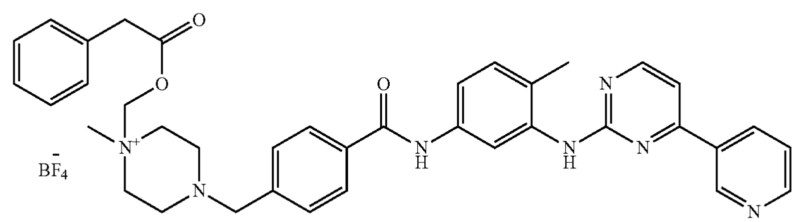 | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium tetrafluoroborate | 643 |
| 10737.06 | 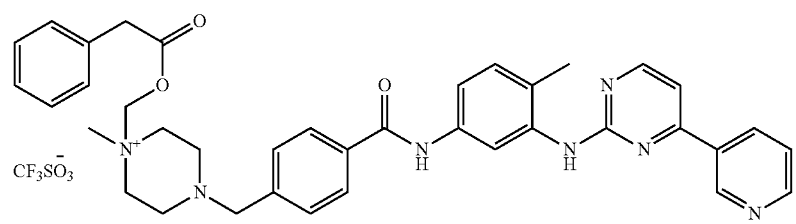 [SMILES: "CF3SO3" ; Cc1ccc(NC(=O)c2ccc(CN3CC[N+](C)(COC(=O)Cc4ccccc4)CC3)cc2)cc1Nc1nccc(-c2cccnc2)n1] | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium trifluoromethanesulfonate | 643 |
| 10737.07 | 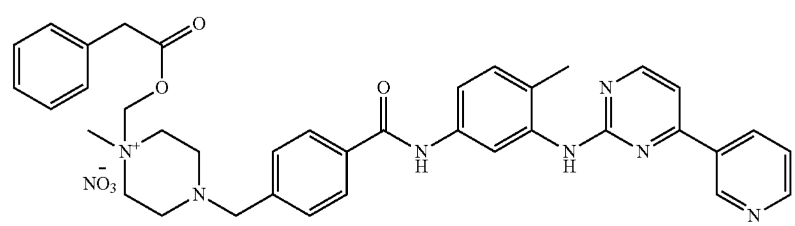 | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium nitrate | 643 |
| 10737.08 | 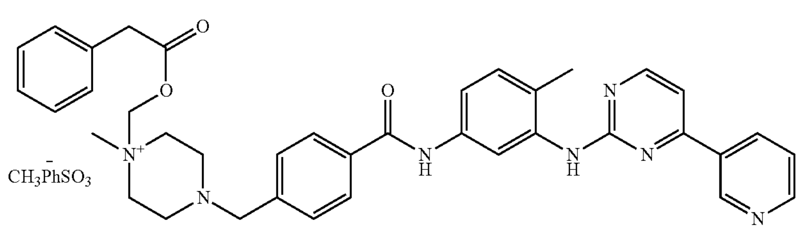 [SMILES: "CH3PhSO3" ; Cc1ccc(NC(=O)c2ccc(CN3CC[N+](C)(COC(=O)Cc4ccccc4)CC3)cc2)cc1Nc1nccc(-c2cccnc2)n1] | 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium p-toluene sulfonate | 643 |
| 11124.01 | 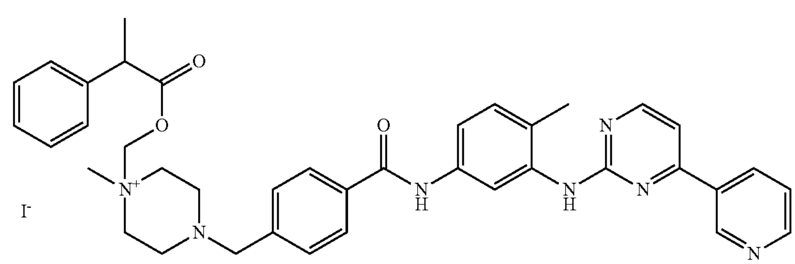 [SMILES: Cc1ccc(NC(=O)c2ccc(CN3CC[N+](C)(COC(=O)C(C)c4ccccc4)CC3)cc2)cc1Nc1nccc(-c2cccnc2)n1 ; [I-]] | 1-methyl-4-(4-((4-methyl-3-((4-(pyridin-3-yl)pyrimidin-2-yl)amino)phenyl)carbamoyl)benzyl)-1-(((2-phenylpropanoyl)oxy)methyl)piperazin-1-ium iodide | 657 |

TABLE 1-continued

| No. | Structure | IUPAC name | m/z |
|---|---|---|---|
| 11124.02 | 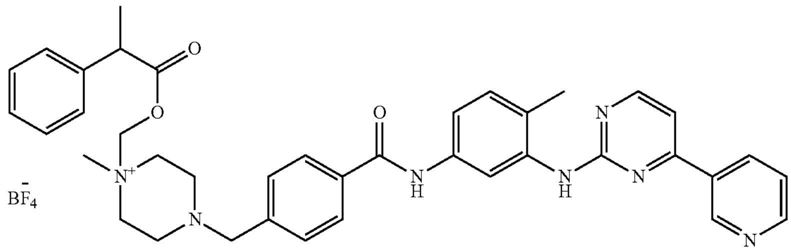 | 1-methyl-4-(4-((4-methyl-3-((4-(pyridin-3-yl)pyrimidin-2-yl)amino)phenyl)carbamoyl)benzyl)-1-(((2-phenylpropanoyl)oxy)methyl)piperazin-1-ium tetrafluoroborate | 657 |
| 11124.03 | 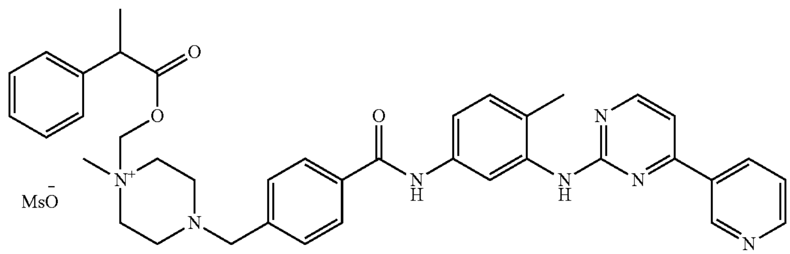 [SMILES: "MsO" ; Cc1ccc(NC(=O)c2ccc(CN3CC[N+](C)(COC(=O)C(C)c4ccccc4)CC3)cc2)cc1Nc1nccc(-c2cccnc2)n1] | 1-methyl-4-(4-((4-methyl-3-((4-(pyridin-3-yl)pyrimidin-2-yl)amino)phenyl)carbamoyl)benzyl)-1-(((2-phenylpropanoyl)oxy)methyl)piperazin-1-ium methanesulfonate | 657 |

A. Synthesis of the Compounds of the Present Invention

The present invention also relates to a process of synthesis of the compounds of the present invention;
The synthesis of the compounds of the present invention may be as enumerated below:

Scheme A: General Scheme for synthesis of the compounds of the present invention:

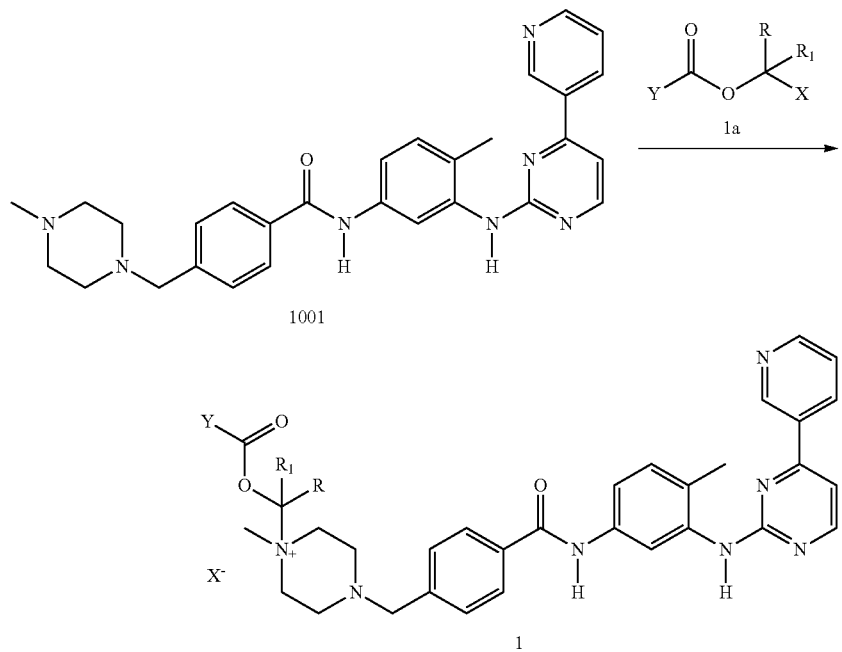

Step 1:—

Imatinib (1001) when reacted with a suitable halomethyl reagent (Type I or II or III) [1a] in a solvent such as DCM at a temperature ranging from room temperature to refluxing followed by evaporation of excess of solvent yield final product [1] which may be further purified to desire level either by crystallization of by washing with a solvent such as ether.

Step 2:—General Scheme for Counter Ion Exchange:

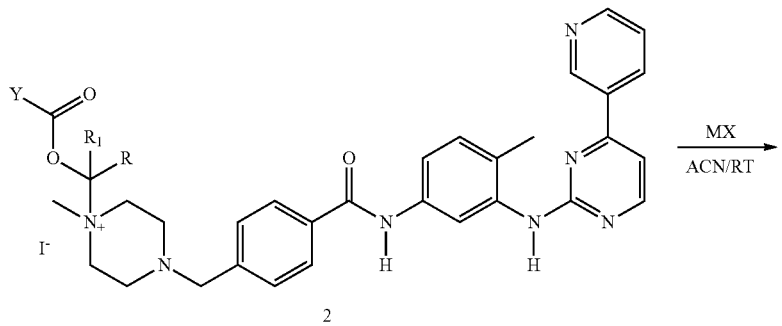

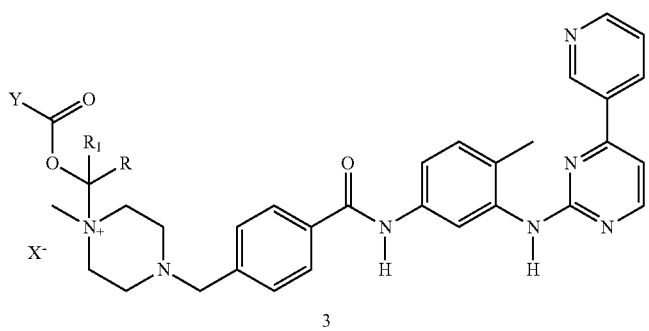

A quaternary salt such as [2] may be prepared by the method describe above in step 1 with a suitable halomethyl formyl reagent such as iodo methyl formyl (Type I or Type II or Type III). Compound [2] may be treated with a suitable metal salt such as silver mesylate in a suitable solvent such as acetonitrile at a desired temperature ranging from ambient to refluxing which results in the precipitation of silver iodide and formation of desired product [3]. The insoluble silver halide maybe filtered out to get reasonably pure desire product [3].

Scheme B:

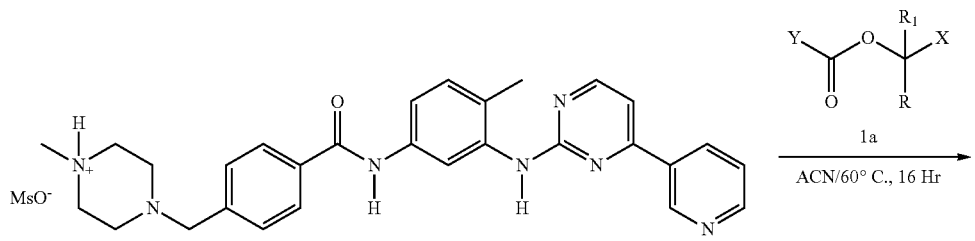

-continued

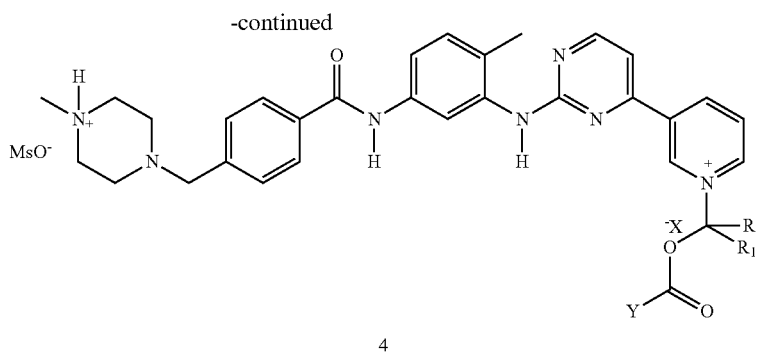

4

Imatinib mesyalte, 1-methyl-4-(4-((4-methyl-3-((4-(pyridin-3-yl)pyrimidin-2-yl)amino)phenyl)carbamoyl)benzyl)piperazin-1-ium methanesulfonate [1026] reacted with suitable halomethyl reagent (Type I or II or III) [1a] in dry solvent such as acetonitrile and at a temperature ranging from room temperature to refluxing followed by evaporation of excess of solvent yield final product [4] which if required can be purified further either by crystallization or by solvent washing with a solvent such as ether.

The above methods are applicable to do anion exchange on all type of quaternary salts having any halide such as chloride, bromide or iodide as the counter ion. The non limiting list of silver salts that may be use includes silver acetate, silver mesylate, silver tosylate, silver oxalate, silver tartrate, silver triflate etc.

The compounds of formula II may be divided in three classes i.e. Type I, where $Y=OR^2$; Type II, where $Y=R^2$ and Type III, where $Y=NR^2R^3$ and may be synthesized by the general schemes as below.

General Methods for the Preparation of Formula II:

The compounds of formula II (Type I, II, III) may be prepared from respective acids, amines and alcohols directly. An acid with or without activation may be reacted with a corresponding aldehyde in presence of a Lewis acid may provide Type II reagent. An alcohol may be reacted with a halomethylhaloformate in presence of a base to provide Type I reagent. Similarly, an amine (primary or secondary) may be reacted with halomethyl haloacetate with or without the presence of base may provide Type III reagent.

General Method to Synthesize Type II Reagents

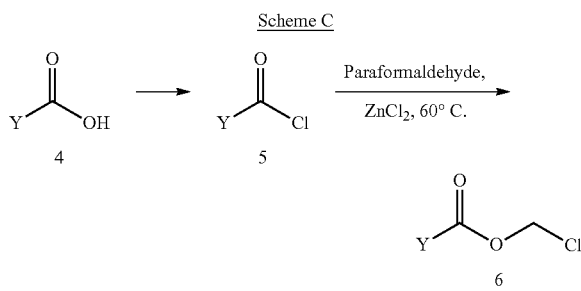

Lewis acids such as zinc chloride (dry), aldehydes such as paraformaldehyde and acid chlorides, [5], may be reacted under anhydrous conditions and at appropriate temperatures, typically between −10° C. and 60° C. for a time ranging up to 24 hours. The reaction mixture may be diluted with solvents such as dichloromethane, washed with aqueous dilute base such as a solution of $Na_2HCO_3$. Standard work up and purifications yield the desired Reagents, [6].

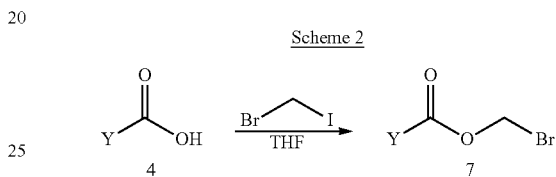

Metal salt of desired acid such as caesium salt of Acid [4], may be treated with bromoiodomethane in Dry THF at appropriate temperatures, typically between 0° C. to RT for 16 hours and if required heating. The reaction mixture may be diluted with solvents such as ethyl acetate, washed with aqueous dilute base such as aqueous solution of $Na_2HCO_3$. Standard work up and purifications yield the desired Reagents [7].

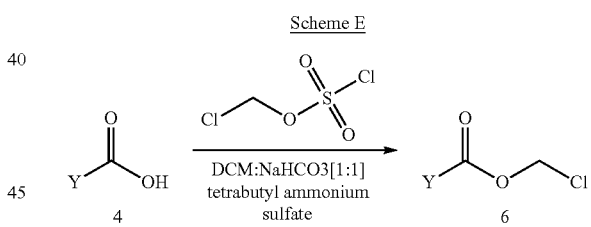

To a vigorously stirred, solution of acid [4] in a solvent such as dichloromethane at room temperature, a base such as sodium bicarbonate and tetrabutylammonium bisulfate in water was added, followed by the drop-wise addition of a solution of chloromethyl chlorosulfate in a solvent such as dichloromethane. After completion of reaction, organic layer was washed with 5% aqueous $Na_2CO_3$. Standard work up and purifications yields desired reagents, [6].

1.

General Method to Synthesize Type III Reagents

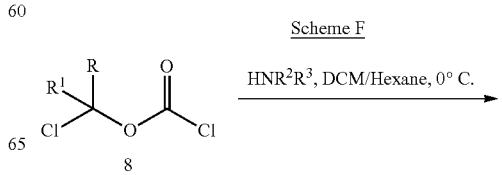

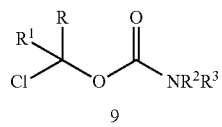

9

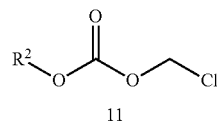

11

Corresponding primary or secondary amines may be reacted with substituted or unsubstituted chloro methylchloroformate, [8], in a solvent such as hexane or DCM at 0° C. The reaction mixture may be filtered and the filtrate may be washed with 1.0 N HCl. The organics may be evaporated to get the desired reagent, [9]. If required, further purification may be achieved using any general purification method practiced in organic chemistry laboratory such as precipitation or crystallization or preparative column purification.

As illustrated above, R and $R^1$ are each independently selected from H, alkenyl, alkynyl, alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are optionally substituted with from 1 to 4 $C_1$-$C_8$ alkyl, alkoxy, aryl and heteroaryl substituents; or R and $R^1$ taken together with the atom to which they are attached form a 3- to 7-membered ring, wherein the 3- to 7-membered ring optionally contains up to two heteroatom groups selected from O, N $R^4$, S, SO and $SO_2$, and is optionally substituted with 1 to 4 alkoxy, F or Cl substituents;

Y is selected from $R^2$, $OR^2$, $NH_2$, $NHR^2$, and $NR^2R^3$;

$R^2$ is selected from alkoxy, aryl, heteroaryl, $C_1$-$C_8$ alkyl and $C_3$-$C_7$ cycloalkyl, wherein in each of said $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl substituents;

$R^3$ is selected from alkoxy, aryl, heteroaryl, $C_1$-$C_8$ alkyl and $C_3$-$C_7$ cycloalkyl, wherein in each of the $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl; or $R^2$ and $R^3$ may be taken together with the nitrogen atom to which they are attached to form a 3- to 7-membered ring, wherein the 3- to 7-membered ring optionally contains up to three heteroatom groups selected from O, $NR^4$, S, SO and $SO_2$, and is optionally substituted with alkoxy, F or Cl.

General Method to Synthesize Type I Reagents

Scheme G

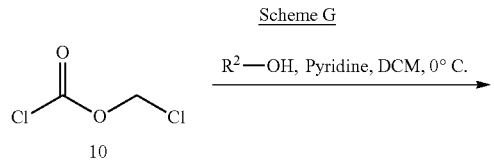

To the solution of chloromethylchloroformate, [10], in a solvent such as hexane, may be added solution of pyridine in hexane, drop wise under ice cooling. To this reaction mixture, the corresponding alcohol may be added at the same temperature. The reaction mixture may be stirred for a time ranging up to 24 hrs. Standard work up and purifications yield the desired corresponding carbonate reagent, [11].

As illustrated above, $R^2$ is selected from alkoxy, aryl, heteroaryl, $C_1$-$C_8$ alkyl and $C_3$-$C_7$ cycloalkyl, wherein in each of said $C_1$-$C_8$ alkyl and $C_3$-$C_7$ cycloalkyl optionally up to three carbon atoms are replaced by a heteroatom group independently selected from O, $NR^4$, S, SO and $SO_2$ (i.e., thereby making a heteroalkyl or heterocyclyl substituent), and wherein the $C_1$-$C_8$ alkyl and $C_3$-$C_7$ cycloalkyl are each optionally substituted with from 1 to 4 $C_1$-$C_8$ alkyl, alkoxy, aryl or heteroaryl substituents.

Scheme H: General Synthetic Scheme for halide exchange:

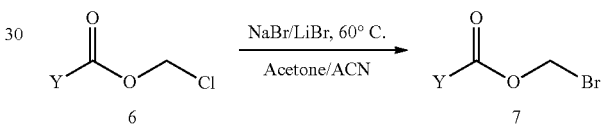

Reagents [6] when treated with bromide suitable reagent such as lithium bromide or sodium bromide at appropriate temperatures, typically in the range of 40-80° C. for a time ranging up to 24 hours followed by standard work up and purification, yields desired bromo Reagents, [7].

Scheme I

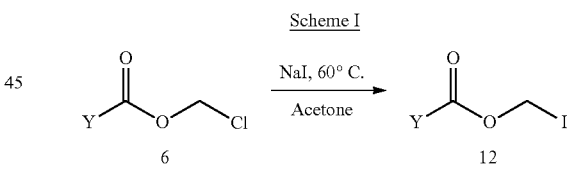

Reagents [6] when treated with a reagent such as sodium iodide at appropriate temperatures, typically ranging from room temperature to 60° C. for a time ranging up to 24 hours followed by a standard work up and purification, yields desired iodo Reagents, [12].

Scheme J

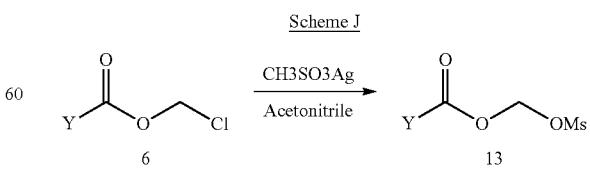

Reagents [6] when treated with silver salt of methane sulfonic acid at appropriate temperatures, typically ranging from room temperature to 60° C. to 90° C. for a time ranging up to 24 hours followed by standard work up and purification, yield desired ((methylsulfonyl)oxy) Reagents, [14].

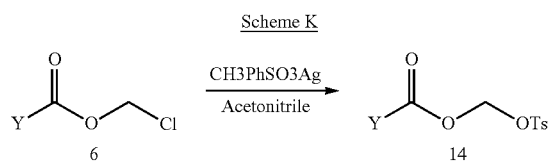

Scheme K

Reagents [6] when treated with silver salt of p-methyl benzene sulfonic acid at appropriate temperatures, typically ranging from room temperature to 60° C. to 90° C. for a time ranging up to 24 hours followed by standard work up and purification yield the desired ((methylsulfonyl)oxy) Reagents, [14].

B. Composition of the Compounds of the Present Invention

The present invention further provides pharmaceutical compositions comprising a compound of formula (I) or its pharmaceutically acceptable salt thereof as an active ingredient along with pharmaceutically acceptable additives/excipients/adjuvants/vehicles. The composition may be administered in a variety of ways including orally, nasally, buccally, sublingually, intravenously, transmucosally, parenterally, by inhalation, spray, transdermally, subcutaneously, intrathecally topically or rectally and may be formulated according to methods known in the art.

The effective dosage form for a mammal may be about 0.1-100 mg/kg of body weight of active compound, which may be administered as a single dose or in the form of individual doses, such as from 1 to 4 times a day.

The mammal may be an adult human.

The compounds of the present invention may optionally be administered with one or more additional drugs. Exemplary additional drugs include one or more compounds independently selected from the group comprising central nervous system drugs, such as cns/respiratory stimulants, analgesics, narcotic agonists, narcotic agonist/antagonists, nonsteroidal anti-inflammatory/analgesic agents, behavior-modifying agents, tranquilizers/sedatives, anesthetic agents, inhalants, narcotics, reversal agents, anticonvulsants, muscle relaxants, skeletal, muscle relaxants, smooth, euthanasia agent, cardiovascular agents, inotropic agents, antiarrhythmic drugs, anticholinergics, vasodilating agents, agents used in treatment of shock, alpha-adrenergic blocking agents, beta-adrenergic blocking agents, respiratory drugs, bronchodilators, sympathomimetics, antihistamines, antitussives, renal and urinary tract, agents for urinary incontinence/retention, urinary alkalinizers, urinary acidifiers, cholinergic stimulants, agents for urolithiasis, gastrointestinal agents, antiemetic agents, antacids, h2 antagonists, gastromucosal protectants, proton pump inhibitors, appetite stimulants, gi antispasmodics-anticholinergics, gastro intestinal stimulants, laxatives, saline, bulk producing, lubricant, surfactant, antidiarrheals, hormones/endocrine/reproductive agents, sex hormones, anabolic steroids, posterior pituitary hormones, adrenal cortical steroids, glucocorticoids, antidiabetic agents, thyroid drugs, thyroid hormones, misc. endocrine/reproductive drugs, prostaglandins, antiinfective drugs, antiparasitics, anticoccidial agents, antibiotics, anti-tuberculosis, aminocyclitols, cephalosporins, macrolides, penicillins, tetracyclines, lincosamides, quinolones, sulfonamides, miscellaneous antibacterials, antifungal agents, antiviral agents, blood modifying agents, clotting agents, anticoagulants, erythropoietic agents, antineoplastics/immunosuppresives, alkylating agents, antidotes, bone/joint agents, dermatologic agents (systemic), vitamins and minerals/nutrients, systemic acidifiers, systemic alkalinizers, anti-cancer agents, antiviral agents, etc.

C. Methods of Use

The present invention further provides a method of prophylaxis and/or treatment of, and/or ameliorating the symptoms of diseases comprising administering a therapeutically effective amount of a compound of formula (I) or pharmaceutically acceptable salts thereof or pharmaceutical compositions comprising the compound of formula (I) as the active ingredient.

The compounds of the present invention are useful as c-ABL1 inhibitors and are useful in all disorders where alteration of the amount of c-ABL1 is required in mammals, including humans. The compounds of the present invention may also act as PGDFR inhibitors in mammals, including humans. The compounds of the present invention may also act as inhibitors of stem cell factor receptor (SCFR), also known as c-Kit, in mammals, including humans.

The compounds of the present invention may be used to treat mammals including humans, suffering from a tumoral disease a dose, effective against tumours.

Imatinib mesylate (Gleevec) has been shown to be effective against poxvirus infections by disabling host proteins essential to the virus life cycle (Nature Medicine, 2005, vol. 11, 7, page 731-739) and without interfering with the acquisition of immune memory (Journal of Virology, 2011, vol. 85, 1, p. 21-31).

Similarly, by targeting the host gene products rather the virus itself, short-term administration of imatinib mesylate may be useful in treating Ebola virus infections (Science Translational Medicine, 2012, vol. 4, 123, page 1-10).

Furthermore, Abl family kinases have been shown to regulate the susceptibility of cells to polyomavirus infection by modulating gangliosides required for viral attachment (Journal of Virology, 2010, vol. 84, 9, p. 4243-4251). Hence, Abl kinase inhibitor, e.g., imatinib mesylate may prove useful as therapeutics of human polyomaviruses.

The present application provides a method for preventing or treating a bacterial infection or a viral infection in a subject using a novel compounds as described herein.

In certain embodiments, the bacterial infection is caused by *Pseudomonas aeruginosa*, *Chlamydia trochomatis*, *Escherichia coli*, *Helicobacter pylori*, *Listeria monocytogenes*, *Salmonella typhimurium*, *Shigella flexneri*, or *Mycobacterium tuberculosis*.

In certain embodiments, *Mycobacterium tuberculosis* causes MDR-tuberculosis or XDR-tuberculosis.

In certain embodiments, the viral infection is caused by a Vaccinia virus, a variola virus, a polyoma virus, a Pox virus, a Herpes virus, a cytomegalovirus (CMV), a human 5 immunodeficiency virus, JC virus, BK virus, Simian virus 40 (SV 40), Monkeypox virus, Ebola virus, Marburg virus, Bunyavirus, Arenavirus, Alphavirus e.g., Venezualan equine encephalitis (VEE), Western equine encephalitis (WEE), Flavivirus, West Nile virus or SARS Coronavirus.

In some embodiments, the compounds described in the present application have improved/maintain desirable safety and toxicity profile relative to imatinib mesylate.

In some embodiments, the compounds described in the present application are more soluble than imatinib mesylate in saline and/or at biologically useful pH ranges.

In some embodiments, the compounds described in the present application have modified rate of conversion and thereby may cause a change in the dosage and/or dosing regimen relative to imatinib mesylate.

In some embodiments, the compounds described in the present application may be such that they are cleaved in certain therapeutically important location(s), thereby enabling specificity and selectivity and or targeted drug delivery.

All of the U.S. Patents and other publications cited herein are expressly incorporated by reference herein in each of their entireties.

From the foregoing description, one of ordinary skill in the art can easily ascertain the essential characteristics of the instant invention, and without departing from the spirit and scope thereof can make various changes and/or modifications of the invention to adapt it to various usages and conditions. Accordingly, these changes and/or modifications are properly, equitably and intended to be, within the full range of equivalence of the claims that follow.

EXAMPLES

Example 1: Synthetic Procedure for the Synthesis an Exemplary Type III Reagent

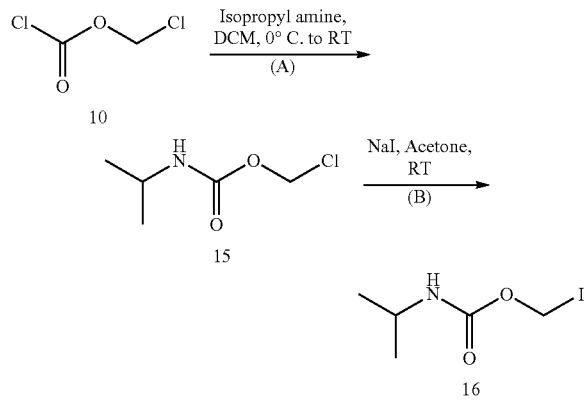

Step (A):

To the solution of chloromethylchloroformate [10] (1.0 g, 7.75 mmol, 1.0 eq) in DCM (y ml) was added a solution of isopropyl amine (0.95 g, 19.30 mmol, 2.5 eq) in DCM drop wise at 0° C. White solid precipitated out in the reaction mixture on addition. The resulting mixture was stirred for 2 hours at 0° C. and then at RT for 1 hour. Reaction was monitored by TLC. The reaction was worked up by diluting the reaction mixture with DCM, washing with saturated NaHCO$_3$ solution, followed by a wash with 2N HCl solution, again washing with saturated NaHCO$_3$ solution, and lastly with water. The organic layer was separated, dried over Na$_2$SO$_4$ and evaporated under reduced pressure to give chloromethyl isopropylcarbamate [15] as colorless oil (0.50 g, 44%).

$^1$H NMR [CDCl$_3$, 300 MHz]: δ 5.73 (s, 2H), 4.73 (s, —NH), 3.78-3.91 (m, 1H), 1.17-1.19 (d, 6H)

Step (B):

Sodium iodide (0.6 g, 3.99 mmol, 3.0 eq) was added to a solution of chloromethyl isopropylcarbamate [15] (0.2 g, 1.33 mmol, 1.0 eq) in acetone. The resulting reaction mixture was stirred at RT overnight. Reaction was monitored by TLC. The reaction was worked up by filtering out precipitated solid and evaporating the acetone layer under vacuum. The solid obtained was dissolved in DCM and filtered to get rid of residual solid. The DCM layer thus obtained was evaporated under reduced pressure to get a crude product, which was purified using silica gel column chromatography (2% MeOH: DCM, 100-200 mesh yield pure iodomethyl isopropylcarbamate [16] as colorless sticky material (0.12 g, 37%). $^1$H NMR [CDCl$_3$, 300 MHz]: δ 5.96 (s, 2H), 4.65 (s, —NH), 3.80-3.91 (m, 1H), 1.17-1.19 (d, 6H).

Example 2

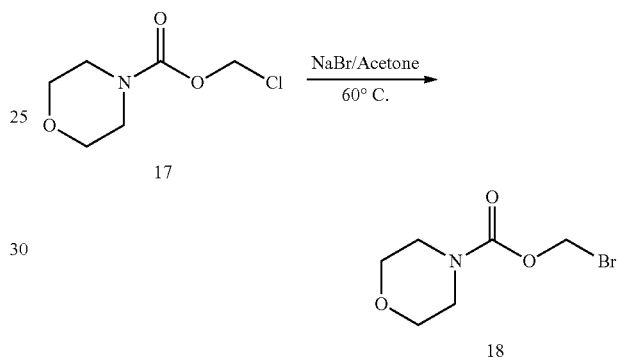

Chloromethyl morpholine-4-carboxylate [17] (0.3 g, 1.67 mmol, 1.0 eq) and sodium bromide (0.86 g, 8.3 mmol, 5.0 eq) was taken in acetone (10 ml). The reaction was refluxed at 60° C. for 24 h. Reaction progress was monitored by TLC/$^1$H NMR. The reaction was filtered off and filtrate was evaporated to dryness under reduced pressure to yield light brown gel, bromomethyl morpholine-4-carboxylate [18] (0.30 g, 80%)

$^1$H NMR (CDCl3): δ ppm 5.92 (s, 2H), 3.72 (t, 4H), 3.54 δ(t, 4H) s

Example 3

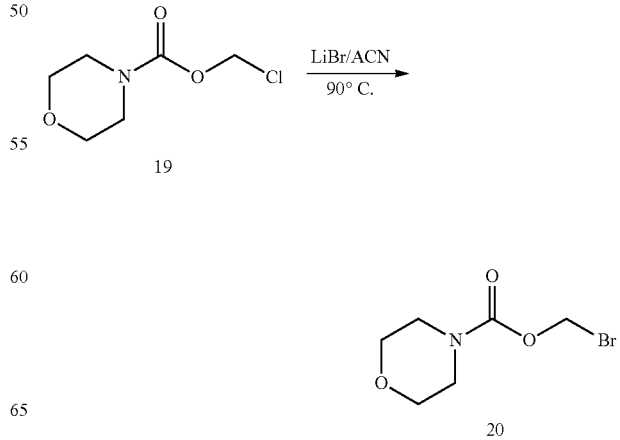

Procedure:

Chloromethyl morpholine-4-carboxylate [19] (0.3 g, 1.67 mmol, 1.0 eq) and lithium bromide (0.72 g, 8.3 mmol, 5.0 eq) was taken in acetonitrile (10 ml). The reaction was refluxed at 90° C. for 30 h. Reaction progress was monitored by TLC/$^1$H NMR. The reaction was filtered off and filtrate was evaporated to dryness under reduced pressure to yield light brown gel, bromomethyl morpholine-4-carboxylate [20] (0.30 g, 80%).

$^1$H NMR (CDCl3): δ ppm 5.92 (s, 2H), 3.72 (t, 4H), 3.54 (t, 4H)

Other methyl formyl reagents were synthesized using the synthetic procedures disclosed above and herein with various substituted or unsubstituted alcohols, phenols, amines and acids to get various structures.

Example 4: Example of a Typical Synthetic Procedure for the Synthesis of Type I Reagents

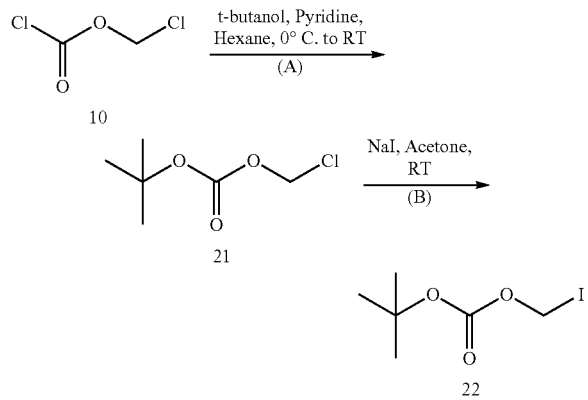

Procedures:
Step (A):

To a solution of chloromethylchloroformate [10] (7.75 mmol, 1 eq) in hexane was added a solution of pyridine (19.3 mmol, 2.5 eq) in hexane drop wise under ice cooling. After the complete addition, a white solid precipitate formed. t-Butanol (11.62 mmol, 1.5 eq) was added in hexane at the same temperature. After the addition of t-butanol the reaction mixture became a clear solution. The resulting mixture was stirred for 2 hours under ice cooling and then 1 hour at room temperature (RT). Reaction completion was monitored by TLC, which showed one non-polar spot compared to starting material. The reaction was worked up by diluting the reaction mixture with hexane and washing with saturated NaHCO3 solution, followed by 2N HCl solution, followed by a second washing with saturated NaHCO3 solution, and lastly by water. The organic layer was separated, dried over Na2SO4 and evaporated under reduced pressure to give the reagent tert-butyl (chloromethyl) carbonate [21] as a colorless sticky liquid (0.900 g, 70%).

$^1$H NMR: [CDCl3, 300 MHz]: −δ 5.774 (s, 2H), 1.518 (s, 9H).

Step (B):

To a solution of tert-butyl (chloromethyl) carbonate [21] (9.87 mmol, 1 eq) dissolved in acetone was added sodium iodide (29.61 mmol, 3 eq). The resulting reaction mixture was stirred overnight at RT. The TLC showed consumption of starting material and one new non polar spot compared to starting material. The reaction was worked up by filtering out any precipitated solid and evaporating the acetone layer. The solid obtained was dissolved in DCM. The solution was filtered once again to eliminate any solid not dissolved in the DCM. The DCM layer obtained was evaporated. The crude product was passed through column chromatography by using 100-200 mesh size silica and 1% MeOH-DCM as a solvent system to yield the product tert-butyl (iodomethyl) carbonate [22] as colorless liquid (136 mg, 30%).

$^1$H NMR [CDCl3, 300 MHz]: δ 5.90 (s, 2H), 1.518 (s, 9H).

Example 5: Synthetic Procedure for an Exemplary Type II Reagent

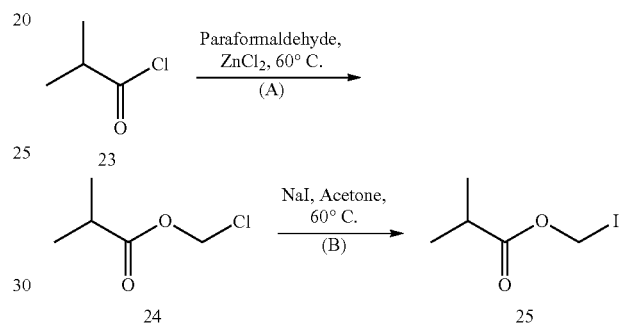

Step (A):

An appropriate Lewis acid such as zinc chloride (catalytic amount ∼0.50 g) was fused in a dried 2-neck round bottomed flask under inert atmosphere. Iso-butyryl chloride [23] (46.72 mmol, 1 eq) and paraformaldehyde (47.0 mmol, 10 eq) are added to the prepared Lewis Acid at RT. The reaction mixture was heated to 60° C. overnight. The reaction was monitored by TLC. The reaction was stopped by addition of DCM and washed with saturated NaHCO3 then brine. The organic layer was separated, dried over Na2SO4 and evaporated under reduced pressure to yield the product, chloromethyl isobutyrate [24], as colorless oil (2.0 g, 31%).

$^1$H NMR [CDCl3, 300 MHz]: δ 5.71-5.76 (d, 2H), 2.54-2.64 (m, 1H), 1.17-1.21 (d, 6H)

Step (B):

Sodium iodide (43.9 mmol, 3 eq) was added to a solution of chloromethyl isobutyrate [24] (14.6 mmol, 1 eq) in acetone. The resulting reaction mixture was stirred at RT overnight. Reaction completion was monitored by TLC. The reaction was worked up by filtering out precipitated solid and evaporation of excess of acetone under reduced pressure. A solid was obtained and washed with DCM while filtering under suction using a Buchner funnel. The DCM layer obtained was evaporated to provide crude product which was further purified using silica gel column chromatography (100-200 mesh) and DCM as an eluent. The product, iodomethyl isobutyrate [25], (1.6 g, 50% yield) was obtained as a brownish liquid.

$^1$H NMR [CDCl3, 300 MHz]: δ 6.21 (s, 2H), 2.54-2.64 (m, 1H), 1.17-1.21 (d, 6H).

Example 6: Synthesis of ((Methylsulfonyl)Oxy)Methyl 3-Methylbutanoate

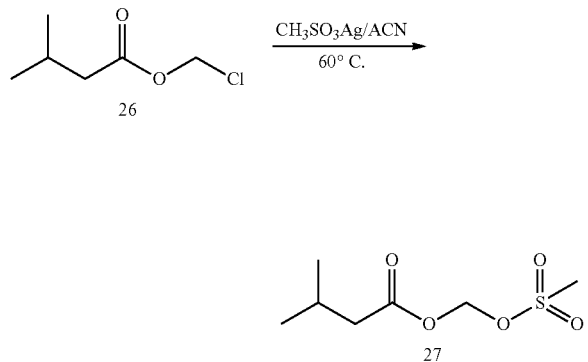

Procedure:

Silver salt of methane sulfonic acid [0.34 g, 1.6 mmol, 0.5 eq] was taken in acetonitrile (8 ml) and chloromethyl 3-methylbutanoate [26] (0.5 g, 3.3 mmol, 1.0 eq) was added to it. The resulting solution was heated to 60° C. temperature ranging from 30 to 80° C., preferably 60° C. for 1 to 10 hour, preferably 5 hour for 5 h. Reaction progress was monitored by TLC. After completion, the reaction was filtered and solvent was evaporated under vacuum to yield colorless oil. The crude compound was purified by silica gel column chromatography (10% EtOAc: CyHex, 100-200 mesh) which afforded [27] ((methylsulfonyl)oxy)methyl 3-methylbutanoate [0.25 g, 40%] as a colorless oil.

Example 6a

Synthesis of ((Methylsulfonyl)Oxy)Methyl 3-Methylbutanoate

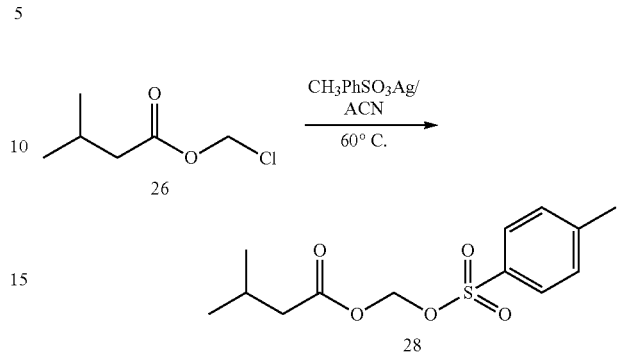

Procedure:

Silver salt of para-toluene sulfonic acid [0.3 g, 1.0 mmol, 0.5 eq] was taken in acetonitrile (8 ml) and chloromethyl 3-methylbutanoate [26] (0.48 g, 3.0 mmol, 1.0 eq) was added to it. The resulting solution was heated to 60° C. temperature ranging from 30 to 80° C., preferably 60° C. for 1 to 10 hour, preferably 5 hour for 5 h. Reaction progress was monitored by TLC. After completion, the reaction was filtered and solvent was evaporated under vacuum to yield colorless oil. The crude compound was purified by silica gel column chromatography (10% EtOAc: CyHex, 100-200 mesh) which afforded [28] ((methylsulfonyl)oxy)methyl 3-methylbutanoate [0.26 g, 35%] as a colorless oil.

Synthesis of Modified Forms of Imatinib

Example 6b

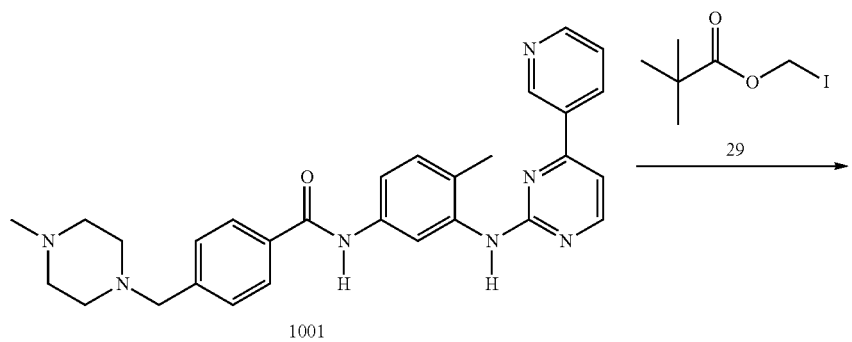

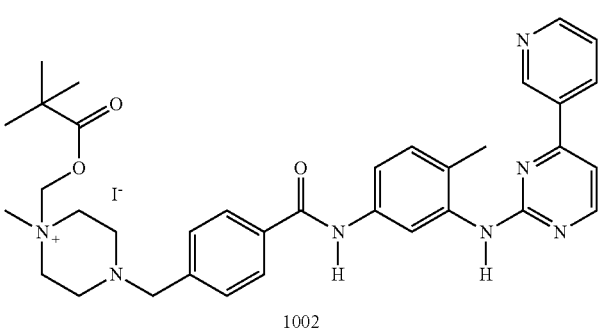

Imatinib, N-(4-methyl-3-((4-(pyridin-3-yl)pyrimidin-2-yl)amino)phenyl)-4-((4-methylpiperazin-1-yl)methyl)benzamide, [1001] (0.100 g, 0.2 mmol, 1.0 eq) was dissolved in dichloromethane (10 ml) in a 25 ml two-necked round-bottomed flask, and iodomethyl pivalate [29] (0.049 g, 0.2 mmol, 1.0 eq) was added at RT. After stirring for 3-4 hours, the precipitate formed was filtered and washed with DCM to give the product, 1-methyl-4-(4-((4-methyl-3-((4-(pyridin-3-yl)pyrimidin-2-yl)amino)phenyl)carbamoyl)benzyl)-1-((pivaloyloxy)methyl)piperazin-1-ium iodide, [1002] as a yellow solid (0.04 g, 27%).

m/z: 608.

$^1$H NMR [DMSO, 300 MHz]: δ ppm 1.24 (s, 9H), 2.20 (s, 3H), 2.7 (m, 4H), 3.10 (s, 3H), 3.07 (s, 3H), 3.48 (br s, 4H), 3.71 (s, 2H), 5.39 (s, 2H), 7.19 (d, 1H), 7.42-7.54 (m, 5H), 7.9 (d, 2H), 8.06 (d, 1H), 8.45-8.52 (m, 2H), 8.60 (dd, 1H), 9.0 (s, 1H), 9.27 (d, 1H), 10.18 (s, 1H)

Example 7

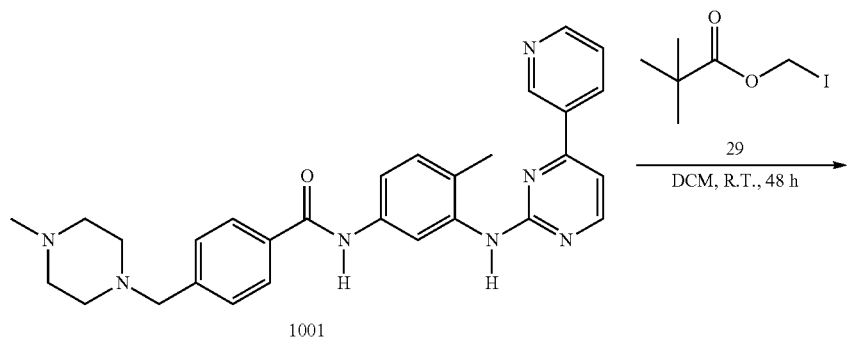

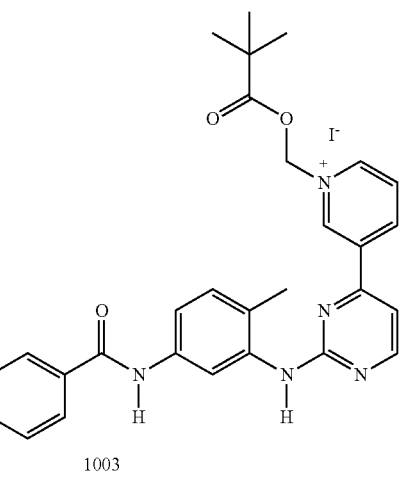

Imatinib [1001] (0.10 g, 0.2 mmol, 1.0 eq) was dissolved in DCM (10 ml) in a 25 ml two-necked round-bottomed flask and iodomethyl pivalate [29] (0.185 g, 0.77 mmol, 3.8 eq) was added while stirring at RT. After 48 h stirring, the precipitate formed was filtered under vacuum and washed with DCM to give the product, 1-methyl-4-(4-((4-methyl-3-((4-(1-((pivaloyloxy)methyl)pyridin-1-ium-3-yl)pyrimidin-2-yl)amino)phenyl)carbamoyl)benzyl)-1-((pivaloyloxy)methyl)piperazin-1-ium diiodide [1003], as a yellow solid (0.05 g, 25%). m/z: 361.

Example 8

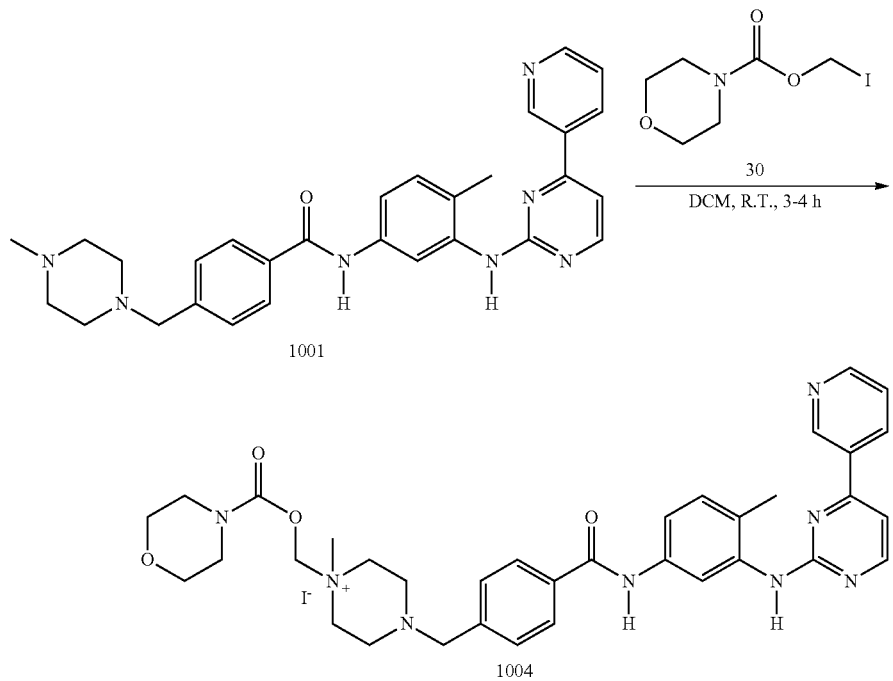

Imatinib, N-(4-methyl-3-((4-(pyridin-3-yl)pyrimidin-2-yl)amino)phenyl)-4-((4-methylpiperazin-1-yl)methyl)benzamide, [1001] (0.100 g, 0.2 mmol, 1.0 eq) was dissolved in dichloromethane (10 ml) in a 25 ml two-necked round-bottomed flask, and iodomethyl carbamate [30] (0.055 g, 0.2 mmol, 1.0 eq) in dichloromethane (5 ml) was added at RT. After stirring for 3-4 hours, the precipitate formed was filtered and washed with DCM to give the product, 1-methyl-4-(4-((4-methyl-3-((4-(pyridin-3-yl)pyrimidin-2-yl)amino)phenyl)carbamoyl)benzyl)-1-(((morpholine-4-carbonyl)oxy)methyl)piperazin-1-ium iodide, [1004] as a yellow solid (0.060 g, 50%). m/z: 637

Example 9

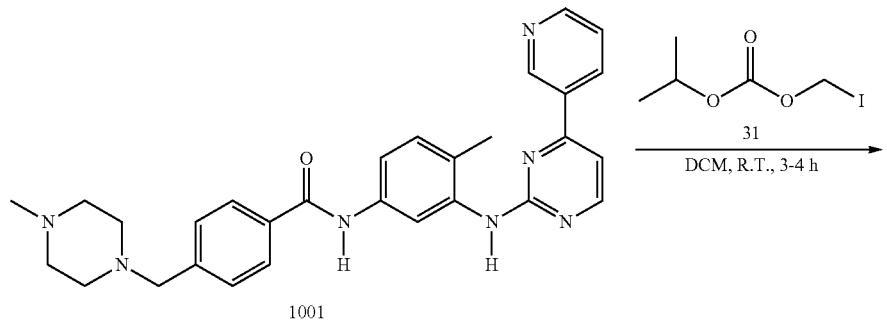

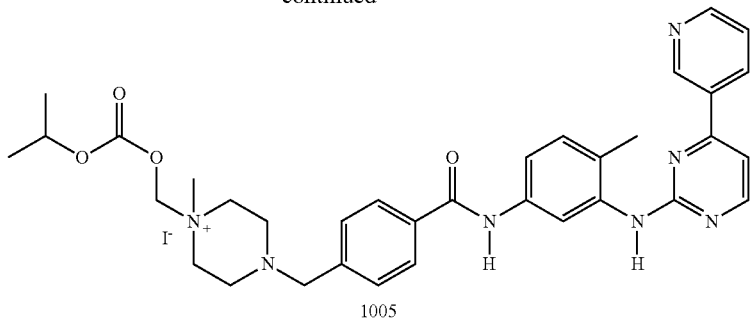

1005

Imatinib, N-(4-methyl-3-((4-(pyridin-3-yl)pyrimidin-2-yl)amino)phenyl)-4-((4-methylpiperazin-1-yl)methyl)benzamide, [1001] (0.100 g, 0.2 mmol, 1.0 eq) was dissolved in dichloromethane (10 ml) in a 25 ml two-necked round-bottomed flask, and iodomethyl isopropyl carbonate [31] (0.047 g, 0.2 mmol, 1.0 eq) in dichloromethane (5 ml) was added at RT. After stirring for 3-4 hours, the precipitate formed was filtered and washed with DCM to give the product, 1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide, [1005] as a yellow solid (0.035 g, 40%). m/z: 610

Example 10

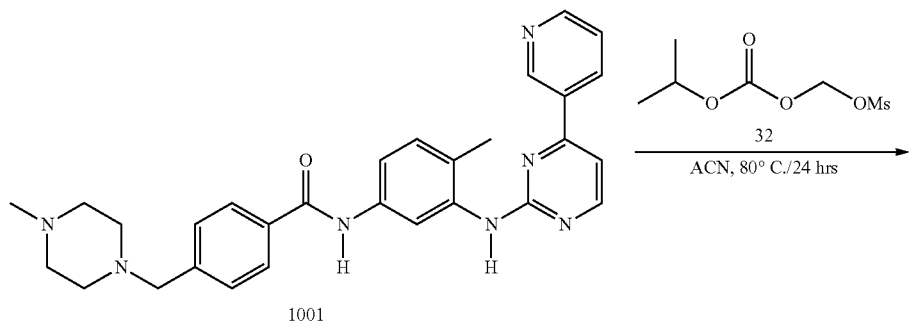

1001

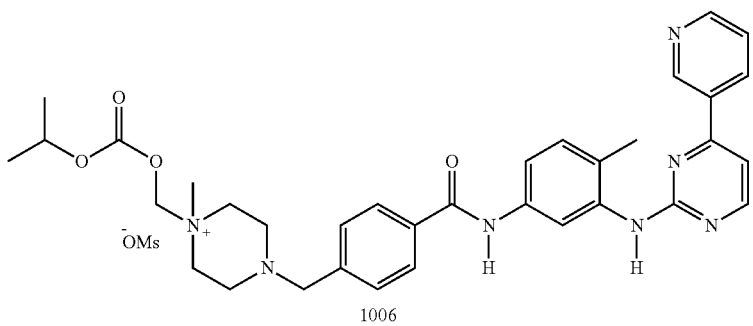

1006

To a suspension of Imatinib, N-(4-methyl-3-((4-(pyridin-3-yl)pyrimidin-2-yl)amino)phenyl)-4-((4-methylpiperazin-1-yl)methyl)benzamide, [1001] (0.100 g, 0.2 mmol, 1.0 eq) in acetonitrile (10 ml) in a 25 ml two-necked round-bottomed flask, and ((isopropoxycarbonyl)oxy)methyl methanesulfonate [32] (0.043 g, 0.2 mmol, 1.0 eq) in acetonitrile (5 ml) was added at RT. The resulting suspension was heated at 80° C. for 24 hrs, The progress of the reaction was monitored by TLC. Then it was cooled to room temperature and evapourated to dryness. The resulting residue was redissolved in dichloromethane (1 ml) and reprecipitated by adding n-pentane, precipitate was filtered and dried to yield crude product, 1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide, [1006] as a yellow solid (0.034 g, 27%). The characterization was done by Mass spectroscopy. m/z: 610

Example 11a

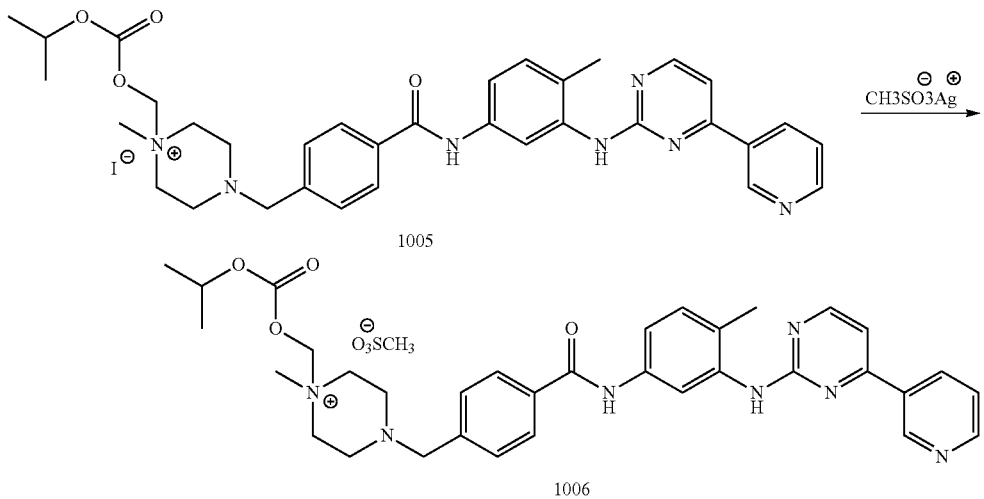

To a stirred solution of (1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium) iodide [1005] (0.0163 g, 0.027 mmol, 1.0 eq) in ACN (2 ml) was added silver(I) methanesulfonate (0.0054 g, 0.027 mmol, 1.0 eq) at RT. The reaction mixture was stirred at RT for 2 h. The reaction was filtered to get rid of silver iodide. Filtrate was concentrated under vacuum, which was triturated with dry ether (2×5 ml), ether removed by decantation and product dried under vacuum to get a pale yellow solid 1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium methane sulfonate [1006] (0.012 g, 66%). m/z: 610

Example 11b

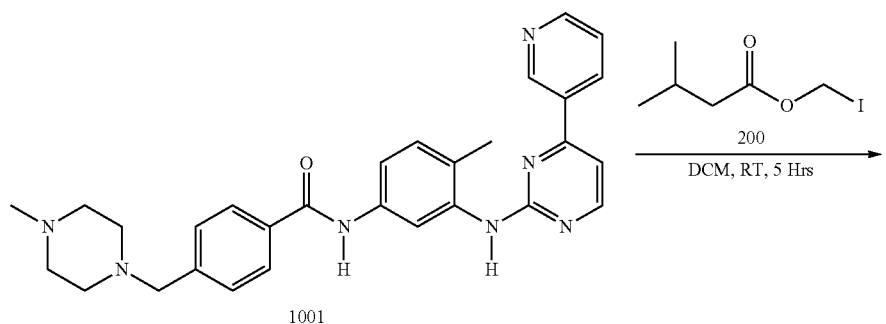

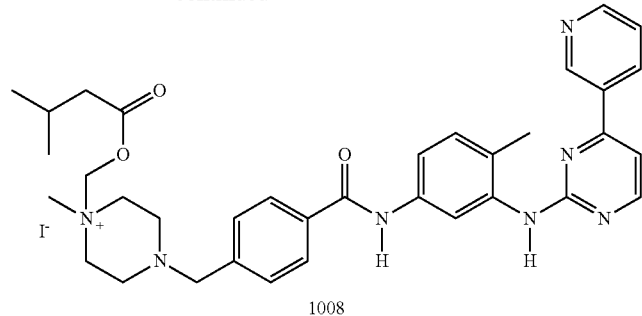

1008

Imatinib [1001] (0.100 g, 0.2 mmol, 1.0 eq) was dissolved in dichloromethane (10 ml) in a 25 ml two-necked RBF followed by addition of iodomethyl 3-methylbutanoate [200] (0.049 g, 0.2 mmol, 1.0 eq) at RT. Reaction mixture was stirred for 4-5 hours, the yellow precipitate thus formed was filtered and washed with DCM to give the product, 1-methyl-4-(4-((4-methyl-3-((4-(pyridin-3-yl)pyrimidin-2-yl)amino)phenyl)carbamoyl)benzyl)-1-(((3-methylbutanoyl)oxy)methyl)piperazin-1-ium iodide [1008] as a yellow solid (0.080 g, 55%). m/z: 608.

Example 12

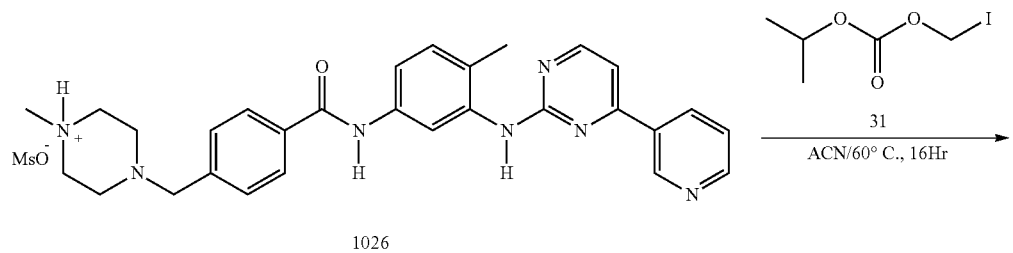

1026

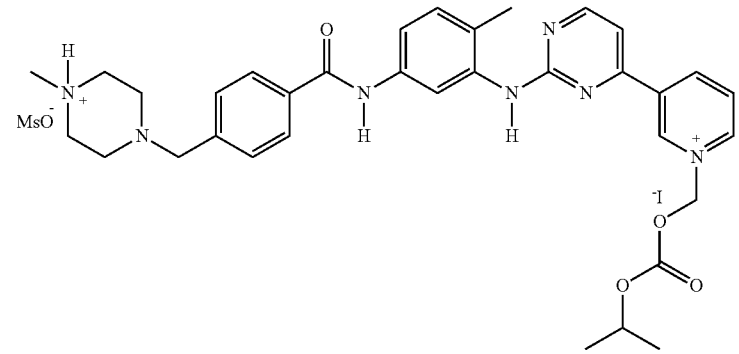

1031

Imatinib mesyalte, 1-methyl-4-(4-((4-methyl-3-((4-(pyridin-3-yl)pyrimidin-2-yl)amino)phenyl)carbamoyl)benzyl)piperazin-1-ium methanesulfonate [1026] (0.100 g, 0.169 mmol, 1.0 eq) was taken in dry acetonitrile (6 ml) in a flame dried 2 neck RB flask equipped with refluxing condenser. To this suspension iodomethyl isopropyl carbonate [31] (0.041 g, 0.169 mmol, 1 eq) was added and heated the reaction mixture at 60° C. for 16 Hrs. During the reaction progress the suspension was turned into a light yellow clear solution. The progress of the reaction was monitored by TLC and $^1$H NMR. After 16 Hrs the solvent was evaporated to dryness and washed the resulting crude reaction mass with diethyl ether (10 ml×2) to give the product, 11-(((isopropoxycarbonyl)oxy)methyl)-3-(2-((2-methyl-5-(4-((4-methylpiperazin-1-yl)methyl)benzamido)phenyl)amino)pyrimidin-4-yl)pyridin-1-iummonoiodide monomethanesulfonate, [1031] as a brown gel (0.105 g, 74%). m/z: 611.

1-methyl-4-(4-((4-methyl-3-((4-(pyridin-3-yl)pyrimidin-2-yl)amino)phenyl)carbamoyl)benzyl)-1-(((3-methylbutanoyl)oxy)methyl)piperazin-1-ium iodide, [1008] was synthesized using (procedure similar to that used for the synthesis of [1002]) using [1001]), iodomethyl 3-methylbutanoate [200] and DCM as solvent.

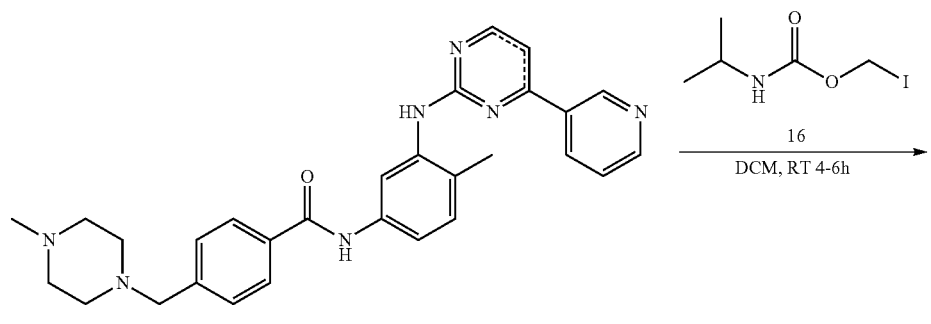

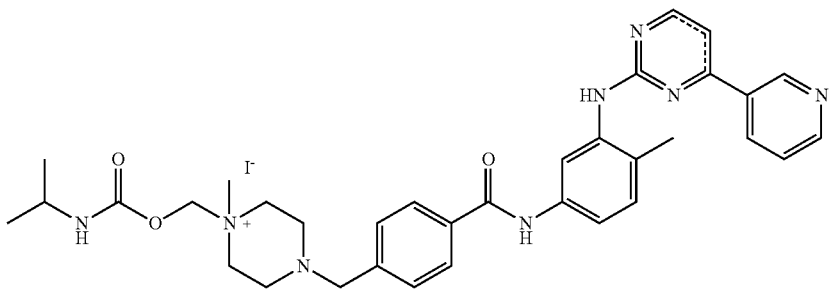

1-(((isopropylcarbamoyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide [1009] was synthesized using (procedure similar to that used for the synthesis of [1002] using [1001]), iodomethyl isopropylcarbamate [16] and DCM as solvent.

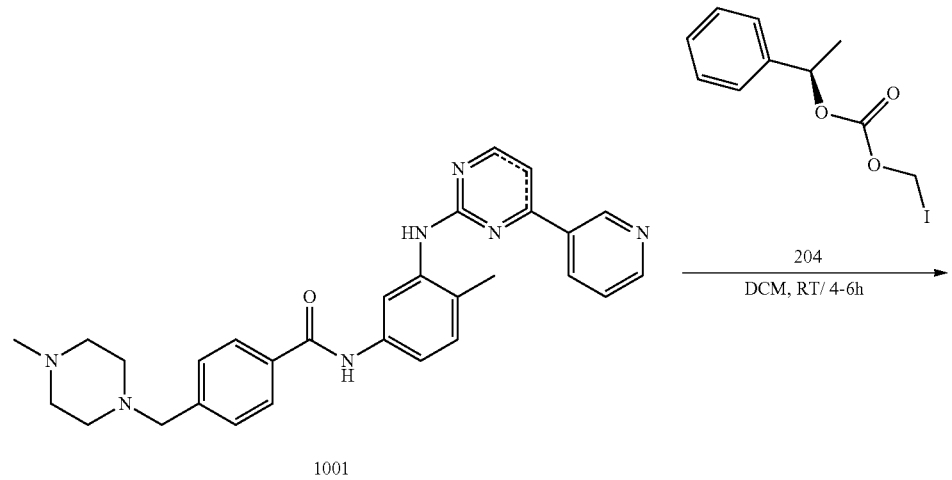

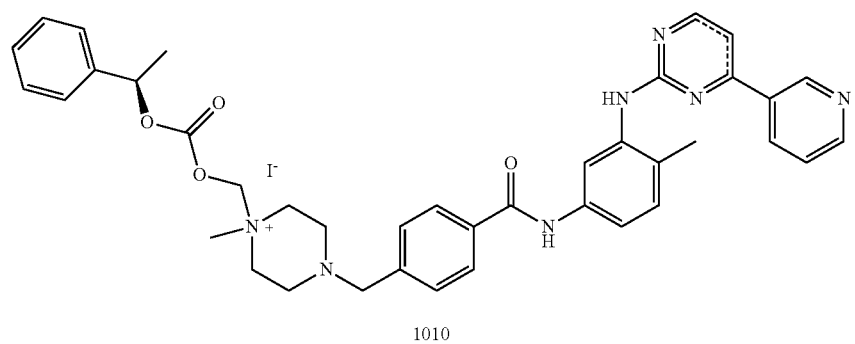

(R)-1-methyl-4-(4-((4-methyl-3-((4-(pyridin-3-yl)pyrimidin-2-yl)amino)phenyl)carbamoyl)benzyl)-1-((((1-phenylethoxy)carbonyl)oxy)methyl)piperazin-1-ium iodide [1010] was synthesized using (procedure similar to that used for the synthesis of [1002] using [1001]), (R)-iodomethyl (1-phenylethyl) carbonate [204] and DCM as solvent.

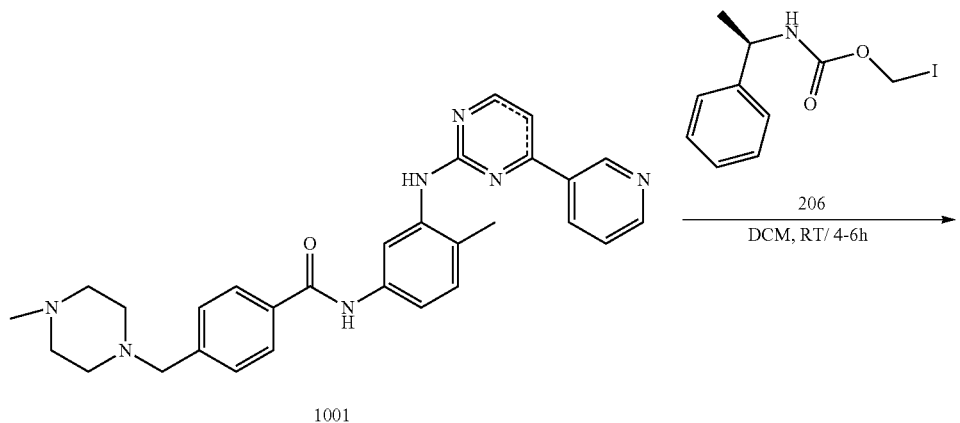

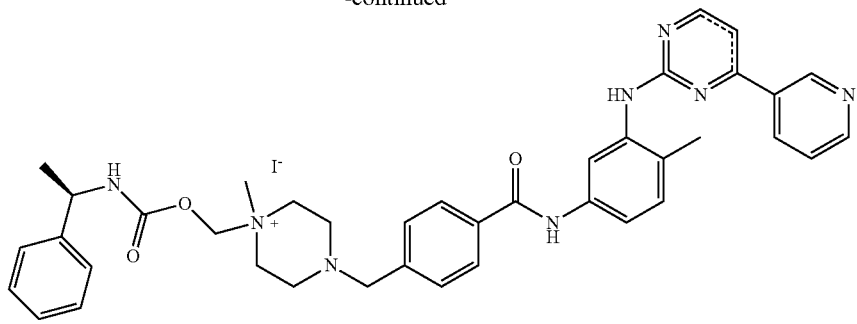
1011
(R)-1-methyl-4-(4-((4-methyl-3-((4-(pyridin-3-yl)pyrimidin-2-yl)amino)phenyl)carbamoyl)benzyl)-1-((((1-phenylethyl)carbamoyl)oxy)methyl)piperazin-1-ium iodide
[1011] was synthesized using (procedure similar to that used for the synthesis of [1002] using [1001]), (R)-iodomethyl (1-phenylethyl)carbamate [206] and DCM as solvent.
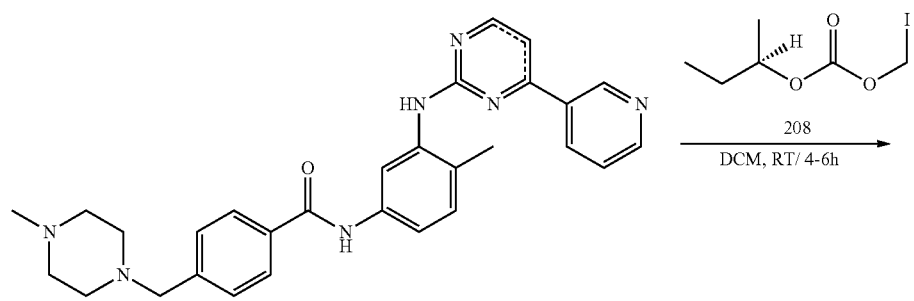
1001
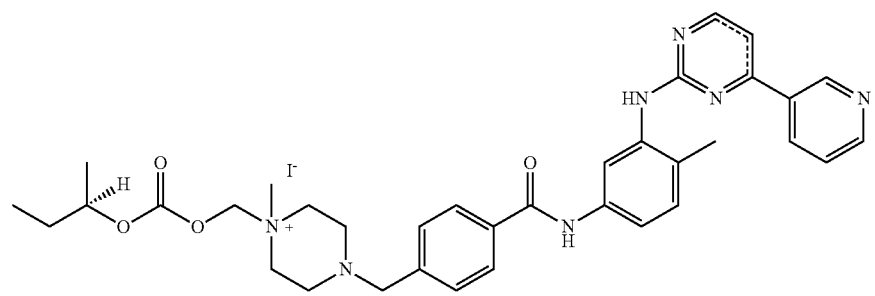
1012

(R)-1-(((sec-butoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide [1012] ] was synthesized using (procedure similar to that used for the synthesis of [1002] using [1001]), (R)-sec-butyl (iodomethyl) carbonate [208] and DCM as solvent.

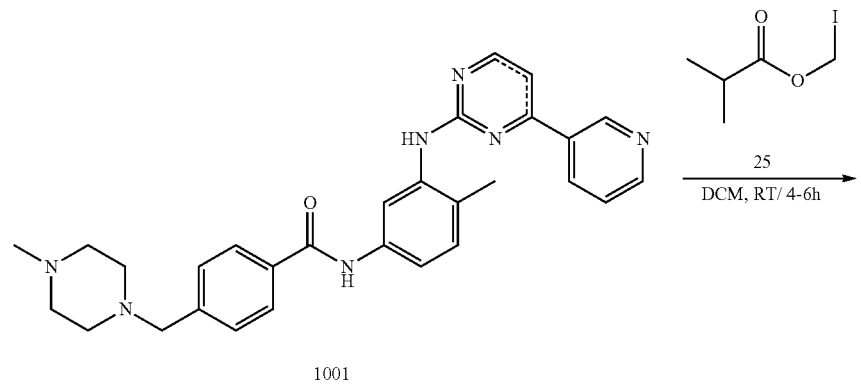

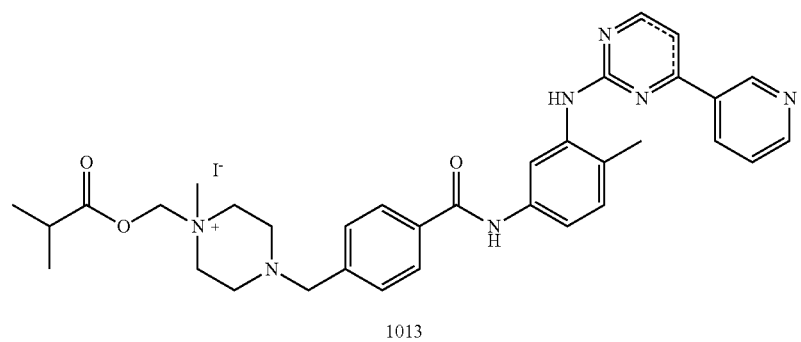

1-((isobutyryloxy)methyl)-1-methyl-4-(4-((4-methyl-3-((4-(pyridin-3-yl)pyrimidin-2-yl)amino)phenyl)carbamoyl)benzyl)piperazin-1-ium iodide [1013] was synthesized using (procedure similar to that used for the synthesis of [1002] using [1001]), iodomethyl isobutyrate [25] and DCM as solvent.

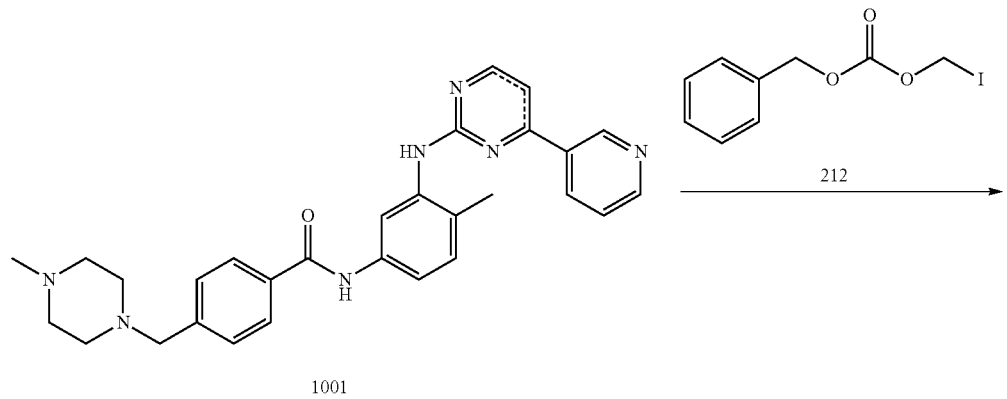

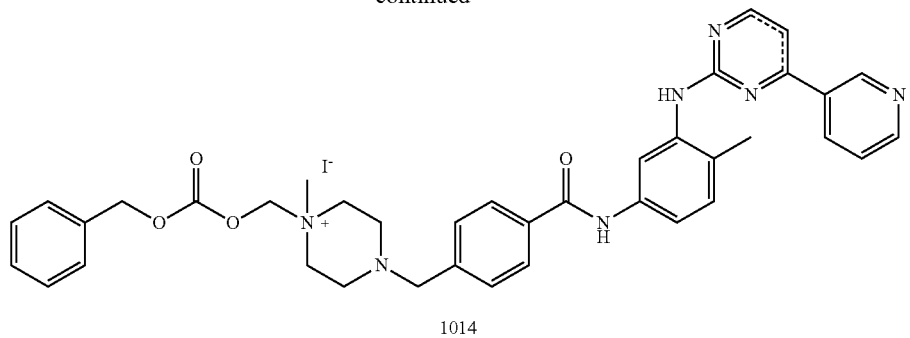
1-((((benzyloxy)carbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide [1014] was synthesized using (procedure similar to that used for the synthesis of [1002] using [1001]), benzyl (iodomethyl) carbonate [212] and DCM as solvent.
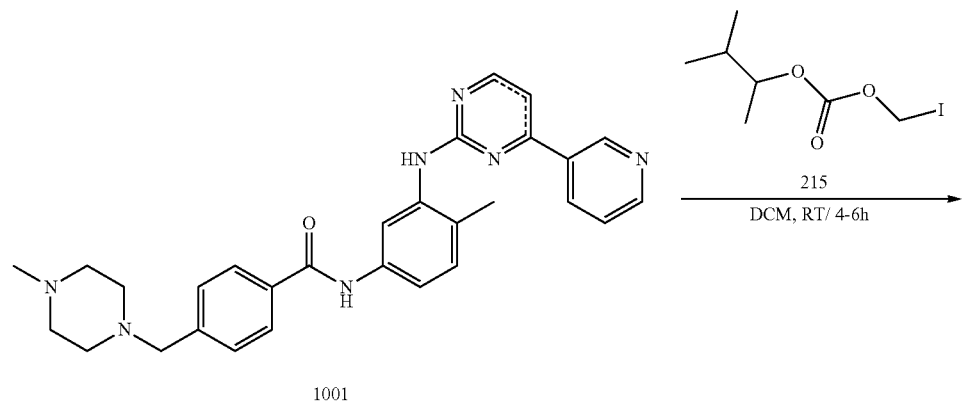
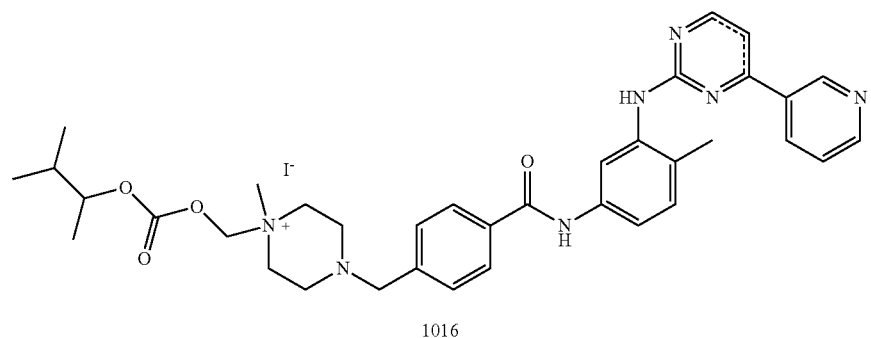

1-methyl-4-(4-(((4-methyl-3-((4-(pyridin-3-yl)pyrimidin-2-yl)amino)phenyl)carbamoyl)benzyl)-1-(((((3-methylbutan-2-yl)oxy)carbonyl)oxy)methyl)piperazin-1-ium iodide [1016] was synthesized using (procedure similar to that used for the synthesis of [1002] using [1001]), iodomethyl (3-methylbutan-2-yl) carbonate [215] and DCM as solvent.

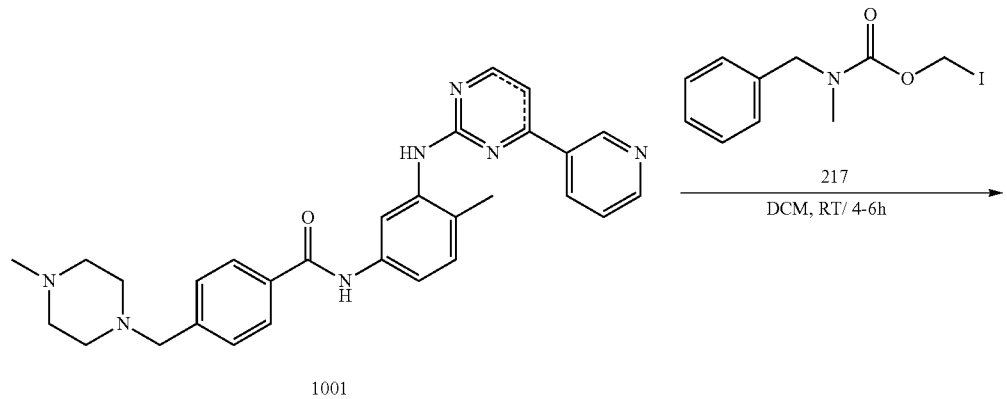

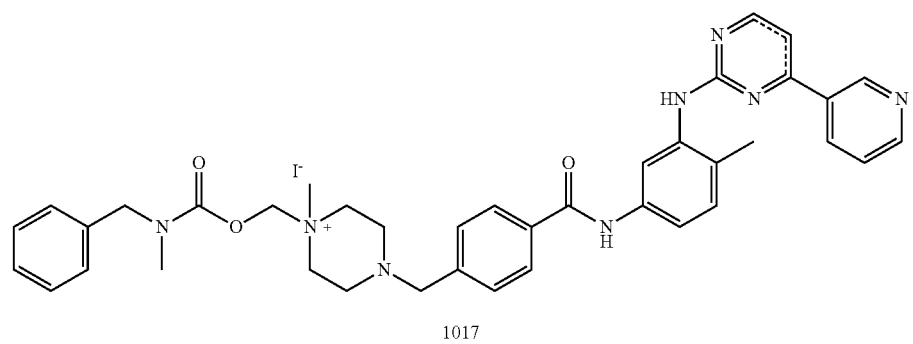

1-(((benzyl(methyl)carbamoyl)oxy)methyl)-1-methyl-4-(4-(((4-methyl-3-((4-(pyridin-3-yl)pyrimidin-2-yl)amino)phenyl)carbamoyl)benzyl)piperazin-1-ium iodide [1017 was synthesized using (procedure similar to that used for the synthesis of [1002] using [1001]), iodomethyl benzyl(methyl)carbamate [217] and DCM as solvent.

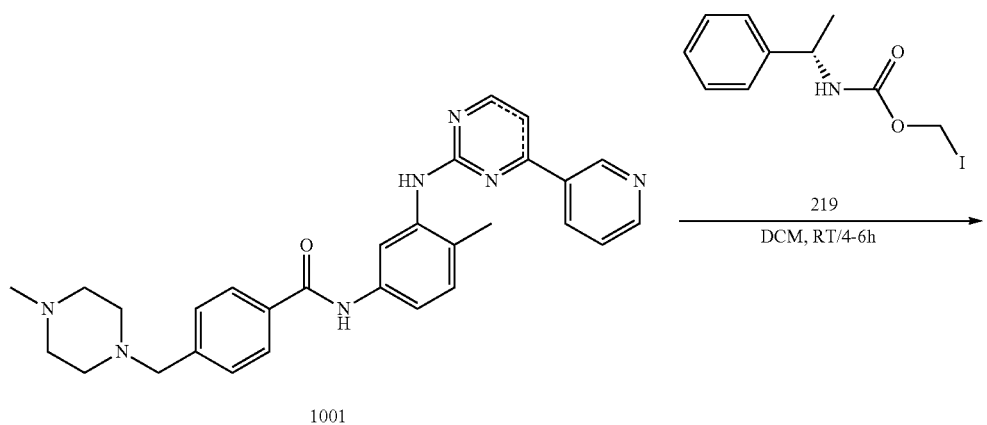

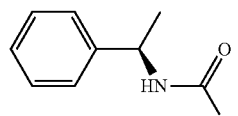
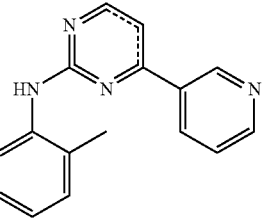
1018
(S)-1-methyl-4-(4-(((4-methyl-3-((4-(pyridin-3-yl)pyrimidin-2-yl)amino)phenyl)carbamoyl)benzyl)-1-((((1-phenylethyl)carbamoyl)oxy)methyl)piperazin-1-ium iodide [1018] was synthesized using (procedure similar to that used for the synthesis of [1002]) using [1001]), (S)-iodomethyl (1-phenylethyl)carbamate [219] and DCM as solvent.
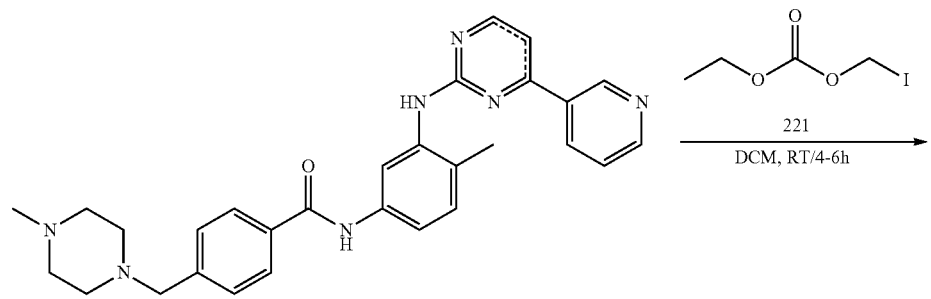
1001
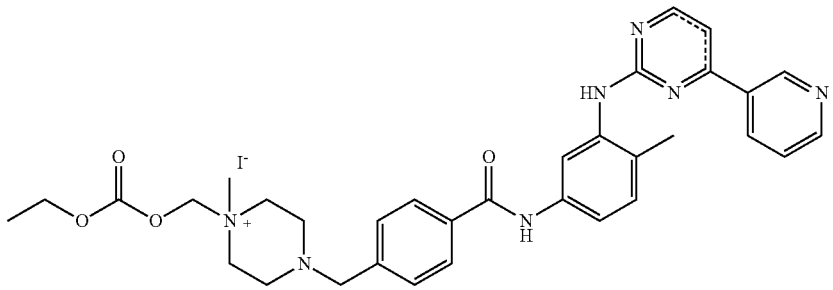
1019

1-(((ethoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide [1019] was synthesized using (procedure similar to that used for the synthesis of [1002]) using [1001]) ethyl (iodomethyl) carbonate [221] and DCM as solvent.

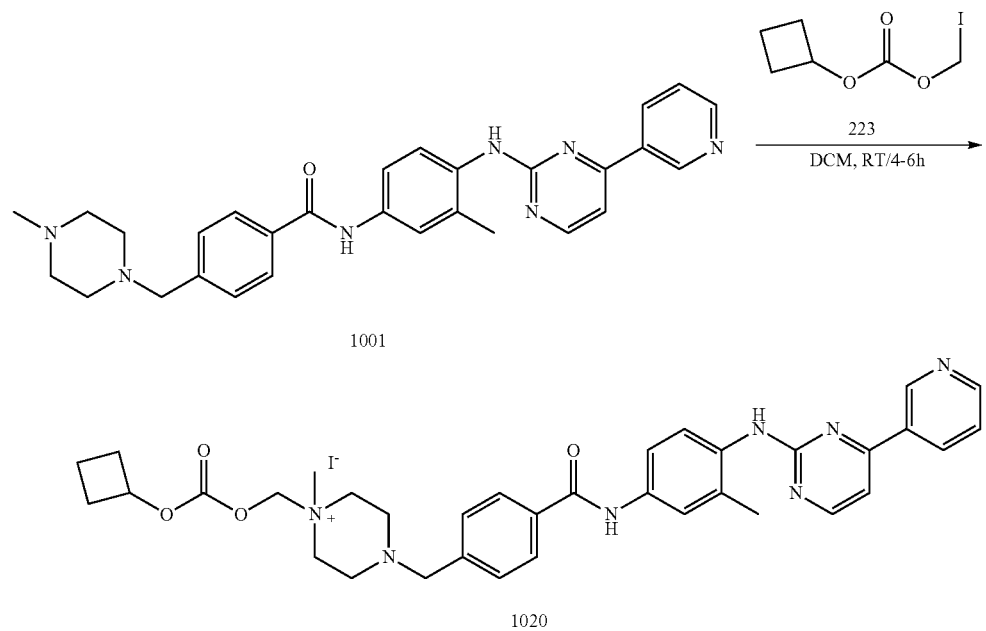

1-(((cyclobutoxycarbonyl)oxy)methyl)-1-methyl-4-(4-((3-methyl-4-((4-(pyridin-3-yl)pyrimidin-2-yl)amino)phenyl)carbamoyl)benzyl)piperazin-1-ium iodide [1020] was synthesized using (procedure similar to that used for the synthesis of [1002] using [1001]), cyclobutyl (iodomethyl) carbonate [223] and DCM as solvent.

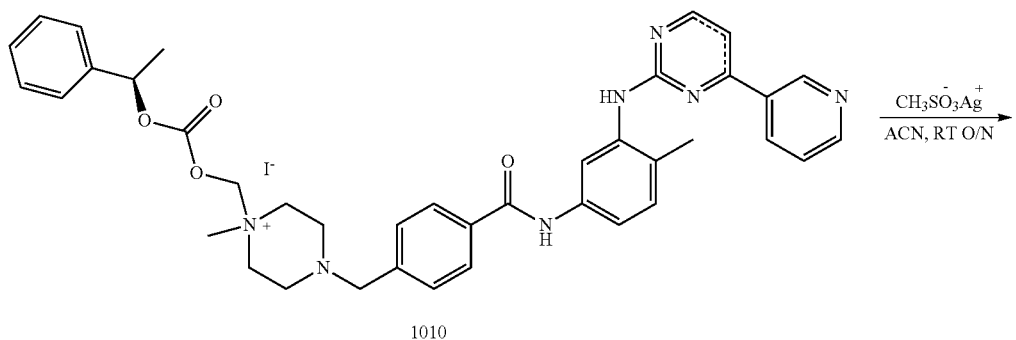

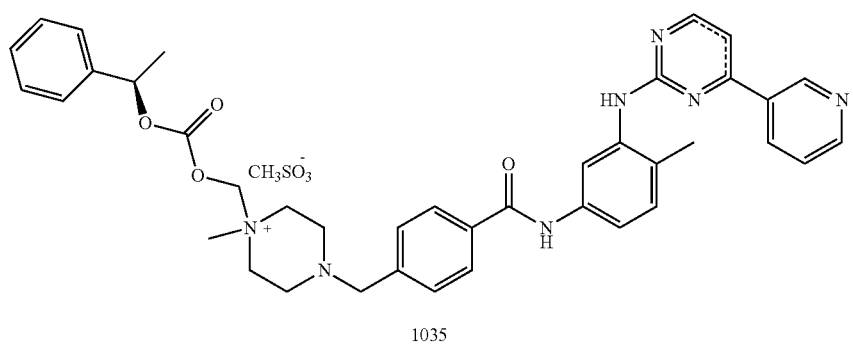

(R)-1-methyl-4-(4-((4-methyl-3-((4-(pyridin-3-yl)pyrimidin-2-yl)amino)phenyl)carbamoyl)benzyl)-1-(((((1-phenylethoxy)carbonyl)oxy)methyl)piperazin-1-ium methanesulfonate [1035] was synthesized using (procedure similar to that used for the synthesis of [1006], using [1005]), Silver methanesulfonate and ACN as solvent.

Example 13: 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium trifluoromethanesulfonate [10737.06]

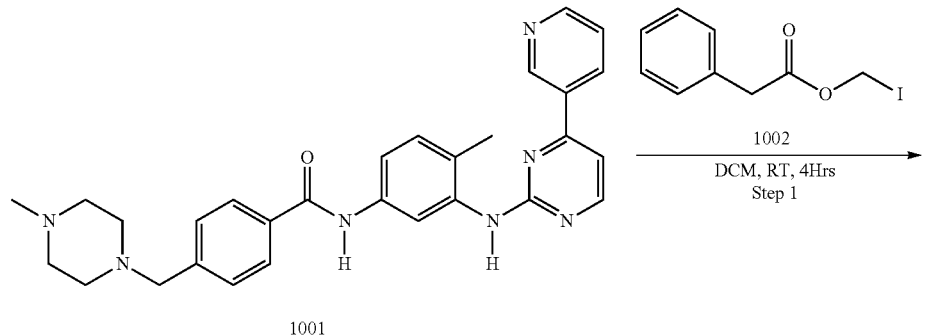

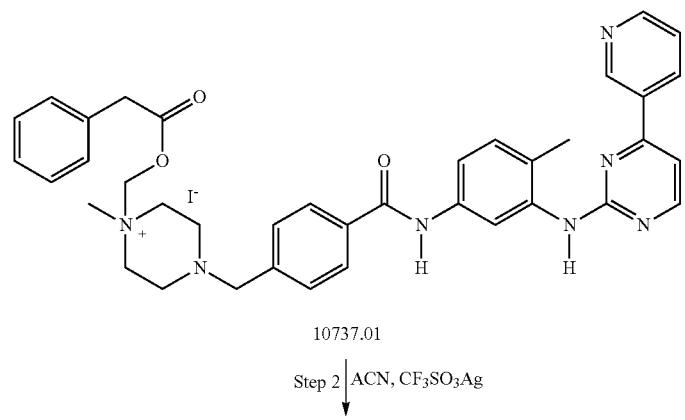

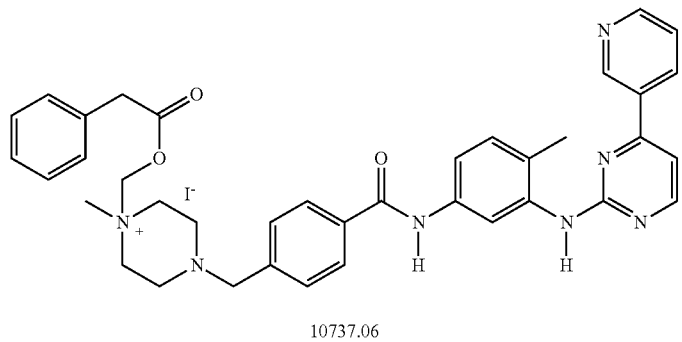

Step 1:

Imatinib, N-(4-methyl-3-((4-(pyridin-3-yl)pyrimidin-2-yl)amino)phenyl)-4-((4-methylpiperazin-1-yl)methyl)benzamide, [1001] (0.5 g, 1.0 mol, 1.0 eq) was dissolved in dry dichloromethane (40 ml) in a 100 ml two-necked round bottom flask, to which was added iodomethyl 2-phenylacetate [1002] (0.28 g, 1.0 mol, 1.0 eq) dissolved in 10 ml DCM dropwise at room temperature. After stirring for 3-4 hours, a yellow precipitate formed. The precipitate was filtered and washed with excess of DCM (dichloromethane) to yield the product, 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium iodide [10737.01] as a yellow solid [0.5 g, 64%]; m/z: 643.

Step 2:

To a stirred solution of 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium iodide [10737.01] (0.08 g, 0.1 mol, 1.0 eq) in CAN [acetonitrile] (10 ml) was added silver(I) trifluoromethane sulfonate (0.026 g, 0.1 mmol, 1.0 eq) at RT. The reaction mixture was stirred at RT for 30 min. The reaction was filtered to get rid of the silver iodide precipitate. The filtrate was concentrated under vacuum, which was triturated with dry ether (2×5 ml). The ether was removed by decantation and the resulting product was dried under vacuum to yield 1-methyl-4-(4-((4-methyl-3-((4-(pyridin-3-yl)pyrimidin-2-yl)amino)phenyl)carbamoyl)benzyl)-1-((2-phenylacetoxy)methyl)piperazin-1-ium trifluoromethanesulfonate [10737.06] as a light yellow solid [0.045 g, 50%]; m/z: 643.

Synthesis of 10737.02, 10737.04, 10737.07, 10737.08 was achieved by using procedure described in Example 13, step 2 above and using the corresponding silver salts (silver nitrate or silver tosylate or silver tetrafluoroborate or silver mesylate etc.) and 10737.01 as starting material.

Synthesis of 11124.01, 11124.02 and 11124.03 was achieved by using the procedure described in Example 13 using iodomethyl 2-phenylpropanoate instead of iodomethyl 2-phenylacetate [1002].

Example 14: Antiviral Potency of Imatinib Against VEE Virus

Primary antiviral screens were conducted to determine EC50 and cellular toxicity to define a therapeutic index by neutral red assay. Secondary assay determines EC90 using more refined concentrations of inhibitor and virus yield reduction. A low level of virus innoculum that produces maximum cell death at a specified time (≥3 days) were used for virus assay, typically 50-100 $CCID_{50}$.

TABLE 1

| Drug | Virus | Virus Family | NIAID Category | Genome Type | EC50 (micromolar) | Therapeutic Index |
|---|---|---|---|---|---|---|
| imatinib | VEE | alphaviridae | B | ssRNA(+) | 6 | 4 |

Example 15: Antiviral Potency of Imatinib Against Polyoma Viruses

PCR amplifications were set up in a reaction volume of 50 μL that contained the TaqMan Universal PCR Master Mix (PE Biosystems), 5 μL of tissue lysate, 300 nmol/L each forward and reverse primer, 200 nmol/L probe, 300 μmmol/L dNTPs, 5 mmol/L magnesium, and 1.25 U of Taq Gold polymerase. Thermal cycling was begun with an initial denaturation step at 95° C. for 12 min that was followed by 45 cycles at 95° C. for 15 s (denaturation) and 60° C. for 1 min (reannealing and extension).

TABLE 2

| Drug | Virus | Genome Type | EC50 (micromolar) | Therapeutic Index |
|---|---|---|---|---|
| imatinib | JCV | dsDNA | 1.25 | 10 |
| imatinib | BKV | dsDNA | 2.1 | 10 |

Pharmacokinetic Properties of the Compounds of the Compounds of the Present Invention The compounds of the present invention were compared for their pharmacokinetic properties with that of imatinib. The data of the compounds are present at Table 3.

PK Protocol

Female Sprague Dawley (SD) rats 3 per group after overnight fasting were dosed orally (via gavage) with imatinib and its modified drugs in distilled water (5 ml/kg) at a dose level of 3 mg/kg. Blood was collected by serial bleeding at 0.16 h, 0.5 h, 1 h, 2 h, 4 h, 6 h, 8 h and 24 h in heparinized tubes. Blood samples were centrifuged at 10,000 rpm for 10 min. at 4° C. to obtain the plasma, which were aspirated into separate labeled tubes and stored at −80° C. 400 ng/ml of Verapamil in acetonitrile was used as the drug extraction solvent for extracting drug from plasma. Extraction solvent was added to plasma was vortexed and shaken on shaker for 10 min, centrifuged at 10000 rpm for 10 min at 4° C. Supernatant was kept for analysis.

Acetonitrile and plasma calibration curves were generated and percentage of imatinib recovery from plasma determined. Quantitative analysis of imatinib levels in each sample was done by liquid chromatography tandem mass spectrometry using multiple reaction monitoring (API3200 LC-MS/MS). $C_{max}$, $T_{max}$, AUC and $t_{1/2}$ were calculated using Graph Pad PRISM version 5.04.

TABLE 3

PK Parameters for compounds
3 mpk, Distilled Water (Rat, triplicate)

| Patent Ref # | AUC (nM*hr) |
|---|---|
| SR-03 (SPR-618) 1006 | 523 |
| SR-05 (SPR_634) | 295 |
| SR-07 (SPR-619) | 470 |
| SR-10 (SPR-631) 1005 | 1574 |
| SR-11 (SPR-621) 1010 | 2712 |
| SR-13.1 (SPR632) 1013 | 356 |
| SR-14* (SPR-136) 1002 | 5233 |
| Standard (SPR-10627) (imatinib) | 1753 |
| 11124.01 | 5102 |

*Vehicle = PEG400

MTS Cell Viability Assay (K562 Cell Line):

The compounds of the present invention were tested for their MTS cell viability assay. The results are presented are Table 4:

K562 cells were the first human immortalised myelogenous leukemia line to be established.

K562 cells are of the erythroleukemia type, and the line is derived from a 53 year old female CML patient. The cells are non-adherent and rounded, are positive for the bcr:abl fusion gene.

K562 cell line is maintained in RPMI1640 with 10% fetal Bovine Serum. 2500 cells/well of K562 cells were plated in 96 well tissue culture plate. Cells were incubated for 48 hours with serially diluted compound (final concentration from 20 μM-0.002 μM) for 48 hr. MTS (3-(4,5-dimethyl-thiazol-2-yl)-5-(3-carboxymethoxyphenyl)-2-(4-sulfophenyl)-2H-tetrazolium), obtained from Promega was added to the wells and plates were incubated at 370 C in 5% CO2 for 4 hrs. The MTS compound is bio-reduced by cells into a colored formazan product that is soluble in tissue culture medium. The quantity of formazan product as measured by the amount of 490 nm absorbance is directly proportional to the number of living cells in culture. The absorbance was read at 490 nm (Spectramax microplate reader). The Percentage inhibition was calculated and plotted against the concentration of inhibitor and data was fit to Non Linear Regression curve fit (sigmoidal dose response curve with variable slope-four parameters) using Graph pad prism 5.

TABLE 4

Activity of the compounds of the present invention in K562 cell lines

| Compound # | % Inhibition—K562 cell line (myelogenous leukemia) | | |
|---|---|---|---|
| | 20 uM | 2 uM | 0.2 uM |
| 1001 | 67 | 64 | 48 |
| 1011 | 70 | 63 | 45 |
| 1028 | 76 | 63 | 40 |

The invention claimed is:

1. A method of treating a tumoral disease, a bacterial infection caused by *Mycobacterium tuberculosis*, or a viral infection caused by a Vaccinia virus, a variola virus, a polyoma virus, a Pox virus, a Herpes virus, a cytomegalovirus (CMV), a human immunodeficiency virus, JC virus, BK virus, Simian virus 40 (SV40), Monkeypox virus, Ebola virus, Marburg virus, Bunyavirus, Arenavirus, Alphavirus, Western equine encephalitis (WEE), Flavivirus, West Nile virus or SARS Coronavirus;

wherein the method comprises:
administering to a human a compound of Formula (I) or a pharmaceutically acceptable salt thereof:

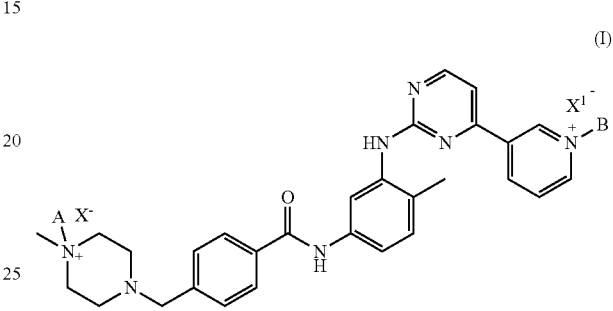

(I)

wherein:
A and B are independently selected from absent, H or a moiety of Formula (II), with the proviso that at least one of A and B is a moiety of Formula (II);

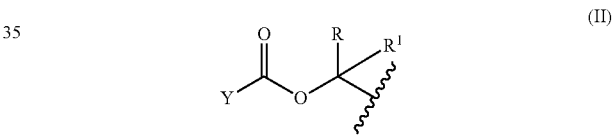

(II)

wherein:
R and $R^1$ are each independently selected from H, alkenyl, alkynyl, alkoxy, aryl, heteroaryl, $C_1$-$C_8$ alkyl or $C_3$-$C_7$ cycloalkyl, wherein in each of the $C_1$-$C_8$ alkyl or $C_3$-$C_7$ cycloalkyl optionally up to three carbon atoms are replaced by a heteroatom group independently selected from O, $NR^4$, S, SO or $SO_2$ (thereby making a heteroalkyl or heterocyclyl substituent), and wherein said $C_1$-$C_8$ alkyl and $C_3$-$C_7$ cycloalkyl are optionally substituted with from 1 to 4 $C_1$-$C_8$ alkyl, alkoxy, aryl or heteroaryl substituents; or R and $R^1$ taken together with the atom to which they are attached form a 3- to 7-membered ring, wherein said 3- to 7-membered ring optionally contains up to two heteroatom groups selected from O, N $R^4$, S, SO or $SO_2$, and is optionally substituted with 1 to 4 alkoxy, F or Cl substituents;

Y, independently for each occurrence, is selected from $R^2$, $OR^2$, $NH_2$, $NHR^2$, or $NR^2R^3$;

$R^2$ is selected from alkoxy, aryl, heteroaryl, $C_1$-$C_8$ alkyl or $C_3$-$C_7$ cycloalkyl, wherein in each of the $C_1$-$C_8$ alkyl or $C_3$-$C_7$ cycloalkyl optionally up to three carbon atoms are replaced by a heteroatom group independently selected from O, $NR^4$, S, SO or $SO_2$ (thereby making a heteroalkyl or heterocyclyl substituent), and wherein said $C_1$-$C_8$ alkyl and $C_3$-$C_7$ cycloalkyl are each optionally substituted with from 1 to 4 $C_1$-$C_8$ alkyl, alkoxy, aryl or heteroaryl substituents;

$R^3$ is selected from alkoxy, aryl, heteroaryl, $C_1$-$C_8$ alkyl or $C_3$-$C_7$ cycloalkyl, wherein in each of the $C_1$-$C_8$ alkyl or $C_3$-$C_7$ cycloalkyl optionally up to three carbon atoms are replaced by a heteroatom group independently selected from O, $NR^4$, S, SO or $SO_2$ (thereby making a heteroalkyl or heterocyclyl substituent), and wherein said $C_1$-$C_8$ alkyl and $C_3$-$C_7$ cycloalkyl are each optionally substituted with from 1 to 4 $C_1$-$C_8$ alkyl, alkoxy, aryl or heteroaryl; or $R^2$ and $R^3$ may be taken together with the nitrogen atom to which they are attached to form a 3- to 7-membered ring, wherein said 3- to 7-membered ring optionally contains up to three heteroatom groups selected from O, $NR^4$, S, SO or $SO_2$, and is optionally substituted with alkoxy, F or Cl;

$R^4$ is, independently for each occurrence, selected from H or $C_1$-$C_8$ alkyl; and X and $X^1$ are, each independently, an anion or absent, provided that X is absent only when A is absent, and $X^1$ is absent only when B is absent;

provided that neither A nor B is

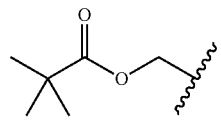

2. The method of claim 1, comprising treating the bacterial infection or the viral infection.

3. The method of claim 2, wherein the infection is bacterial and is caused by *Mycobacterium tuberculosis*.

4. The method of claim 2, wherein the infection is viral and is caused by a Vaccinia virus, a variola virus, a polyoma virus, a Pox virus, a Herpes virus, a cytomegalovirus (CMV), a human immunodeficiency virus, JC virus, BK virus, Simian virus 40 (SV40), Monkeypox virus, Ebola virus, Marburg virus, Bunyavirus, Arenavirus, Alphavirus, Western equine encephalitis (WEE), Flavivirus, West Nile virus or SARS Coronavirus.

5. The method of claim 1, wherein the compound is administered orally, nasally, buccally, sublingually, intravenously, transmucosally, rectally, topically, transdermally, subcutaneously, by inhalation, or intrathecally.

6. The method of claim 1, wherein R and $R^1$ are each independently selected from H or $C_1$-$C_8$ alkyl.

7. The method of claim 1, wherein R and $R^1$ are both H.

8. The method of claim 1, wherein $R^2$ and $R^3$ are independently selected from $C_1$-$C_8$ alkyl or aralkyl.

9. The method of claim 8, wherein $R^2$ and $R^3$ are independently selected from methyl, ethyl, isopropyl, tert-butyl, isobutyl, sec-butyl, 3-methylbut-2-yl, 1-phenylethyl, benzyl or cyclobutyl.

10. The method of claim 1, wherein $R^4$, independently for each occurrence, is selected from H or $C_1$-$C_8$ alkyl.

11. The method of claim 1, wherein X and $X^1$ are each independently halide or sulfonate.

12. The method of claim 1, wherein A is a moiety of Formula (II) and B is absent.

13. The method of claim 1, wherein A is absent and B is a moiety of Formula (II).

14. The method of claim 1, wherein Y, independently for each occurrence, is $OR^2$.

15. The method of claim 14, wherein the moiety of Formula (II), independently for each occurrence, is a moiety that would remain after displacing chlorine from:

i. chloromethyl isopropyl carbonate;
ii. benzyl chloromethyl carbonate;
iii. chloromethyl morpholinomethyl carbonate;
iv. chloromethyl isobutyl carbonate;
v. chloromethylmethyl carbonate;
vi. (S)-sec-butyl chloromethyl carbonate;
vii. (R)-sec-butyl chloromethyl carbonate;
viii. chloromethyl ((3S,5R)-3,5-dimethylmorpholino) methyl carbonate;
ix. chloromethyl 2-methylcyclopropyl carbonate;
x. chloromethyl 2-methoxy ethyl carbonate;
xi. chloromethyl propyl carbonate;
xii. chloromethyl cyclobutyl carbonate;
xiii. chloromethyl cyclopropyl carbonate;
xiv. chloromethyl 2,2-dimethylcyclobutyl carbonate;
xv. chloromethyl cyclopentyl carbonate;
xvi. chloromethyl oxetan-3-yl carbonate;
xvii. (S)-chloromethyl tetrahydrofuran-3-yl carbonate;
xviii. chloromethyl cyclohexylmethyl carbonate;
xix. chloromethyl 3-methoxycyclohexyl carbonate;
xx. (R)-chloromethyl tetrahydrofuran-3-yl carbonate;
xxi. chloromethyl ethoxymethyl carbonate;
xxii. chloromethyl oxepan-4-yl carbonate;
xxiii. (1R,2S,4S)-bicyclo[2.2.1]heptan-2-yl chloromethyl carbonate;
xxiv. chloromethyl 2,3-dihydro-1H-inden-1-yl carbonate;
xxv. benzyl chloromethyl carbonate;
xxvi. (S)-chloromethyl 1-phenylethyl carbonate;
xxvii. chloromethyl cyclohexyl carbonate;
xxviii. chloromethyl isobutyl carbonate;
xxix. chloromethyl 4-methylcyclohexyl carbonate;
xxx. chloromethyl 2-(methylthio)ethyl carbonate;
xxxi. chloromethyl 3-methylcyclohexyl carbonate;
xxxii. chloromethylpentan-2-yl carbonate;
xxxiii. chloromethyl neopentyl carbonate;
xxxiv. methyl 1-((chloromethoxy)carbonyloxy)cyclopropanecarboxylate;
xxxv. chloromethyl cyclopropylmethyl carbonate;
xxxvi. chloromethyl 2,2-diethoxyethyl carbonate;
xxxvii. chloromethyl cyclopentylmethyl carbonate;
xxxviii. methyl 2-((chloromethoxy)carbonyloxy)propanoate;
xxxix. (S)-chloromethyl 2,2,4-trimethylcyclopent-3-enyl carbonate;
xl. chloromethyl 1,3-dioxolan-2-yl carbonate;
xli. chloromethyl (2,6-dimethylcyclohexyl)methyl carbonate;
xlii. chloromethyl 2-(tetrahydro-2H-pyran-2-yl)ethyl carbonate;
xliii. chloromethyl(tetrahydro-2H-pyran-4-yl)methyl carbonate;
xliv. chloromethyl tetrahydro-2H-pyran-4-yl carbonate;
xlv. chloromethyl 1-methylcyclopentyl carbonate;
xlvi. chloromethyl 1-cyclopentylethyl carbonate;
xlvii. chloromethyl 3-methylcyclopentyl carbonate;
xlviii. chloromethyl 3,3-dimethylcyclohexyl carbonate;
xlix. chloromethyl 2,5-dimethylcyclohexyl carbonate;
l. chloromethyl 1-(4-methylcyclohexyl)ethyl carbonate;
li. chloromethyl (3-methyloxetan-3-yl)methyl carbonate;
lii. chloromethyl (3-methyloxetan-3-yl)methyl carbonate;
liii. chloromethyl 2-isopropoxyethyl carbonate;
liv. (chloromethyl carbonic) 5-((3aS,4S,6aR)-2-oxohexahydro-1H-thieno[3,4-d]imidazol-4-yl)pentanoic anhydride;
lv. 4-((chloromethoxy)carbonyloxy)-2-hydroxy-4-oxobutanoic acid;
lvi. chloromethyl 4-formyl-2-methoxyphenyl carbonate;

lvii. chloromethyl 3-oxobutan-2-yl carbonate;
lviii. methyl 4-((chloromethoxy)carbonyloxy)benzoate;
lix. (R)-2-amino-3-((chloromethoxy)carbonyloxy)propanoic acid;
lx. 3-tert-butyl-4-methoxyphenyl chloromethyl carbonate;
lxi. (R)-2-amino-3-(4-((chloromethoxy)carbonyloxy)phenyl)propanoic acid;
lxii. (R)-2-amino-4-((chloromethoxy)carbonyloxy)-4-oxobutanoic acid;
lxiii. (E)-chloromethyl 3,7-dimethylocta-2,6-dienyl carbonate;
lxiv. methyl 4-((chloromethoxy)carbonyloxy)benzoate;
lxv. chloromethyl 2-(4-methylcyclohex-3-enyl)propan-2-yl carbonate;
lxvi. chloromethyl 3,7-dimethylocta-1,6-dien-3-yl carbonate;
lxvii. 4-allyl-2-methoxyphenyl chloromethyl carbonate;
lxviii. chloromethyl (1R,2S,5R)-2-isopropyl-5-methylcyclohexyl carbonate;
lxix. propyl 4-((chloromethoxy)carbonyloxy)benzoate; or
lxx. (E)-chloromethyl 3,7-dimethylocta-2,6-dienyl carbonate.

16. The method of claim 15, wherein the moiety of Formula (II), independently for each occurrence, is a moiety that would remain after displacing chlorine from (S)-sec-butyl chloromethyl carbonate or (R)-sec-butyl chloromethyl carbonate.

17. The method of claim 1, wherein the compound of Formula (I) is represented by Formula (III) or Formula (IV):

Formula (III)

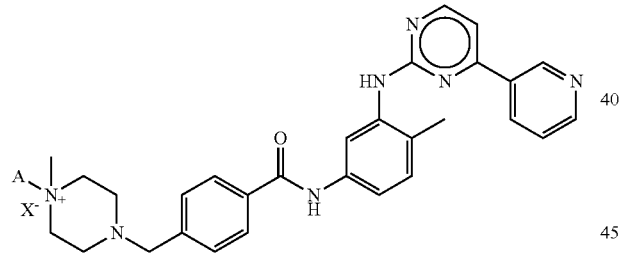

Formula (IV)

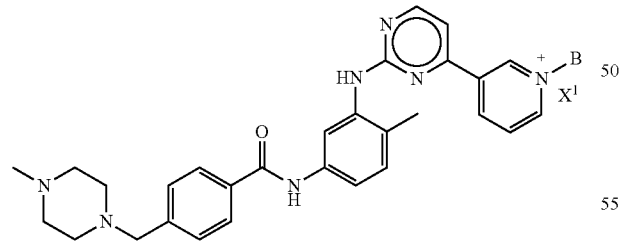

where A or B is selected from compounds 101 to 120:

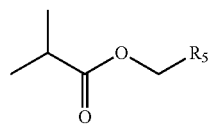
101

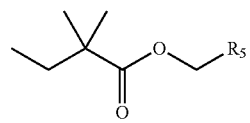
102

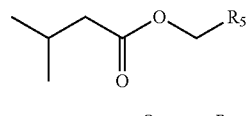
103

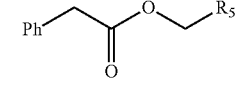
104

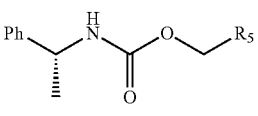
105

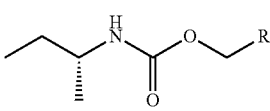
106

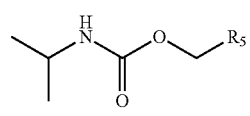
107

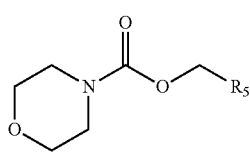
108

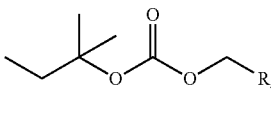
109

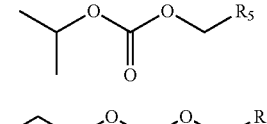
110

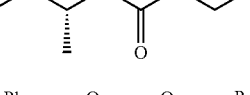
111

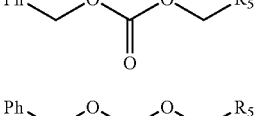
112

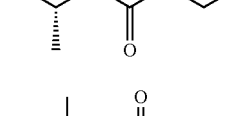
113

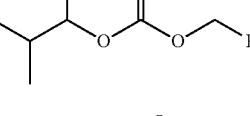
116

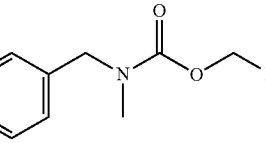
117

-continued

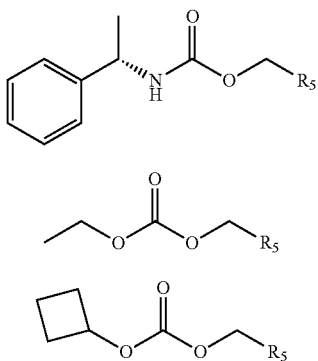

118

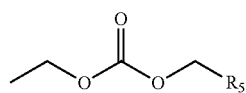

119

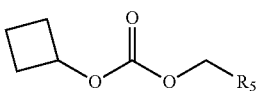

120 where $R^5$ represents a nitrogen atom of the imatinib moiety linked to A or B; and X can be iodide, chloride, bromide, mesylate, tosylate, or any other pharmaceutically acceptable anion.

18. The method of claim 17, wherein A or B is selected from compound 111.

19. The method of claim 17, wherein the compound of Formula (III) or Formula (IV) is selected from:

1-methyl-4-(4-((4-methyl-3-((4-(pyridin-3-yl)pyrimidin-2-yl)amino)phenyl)carbamoyl)benzyl)-1-(((morpholine-4-carbonyl)oxy)methyl)piperazin-1-ium iodide;

1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium iodide;

1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium methane sulfonate;

1-(((isopropoxycarbonyl)oxy)methyl)-1-methyl-4-(4-((4-methyl-3-((4-(pyridin-3-yl)pyrimidin-2-yl)amino)phenyl)carbamoyl)benzyl)piperazin-1-ium p-tolyl sulfonate;

1-methyl-4-(4-(4-methyl-3-(4-(pyridin-3-yl)pyrimidin-2-ylamino)phenylcarbamoyl)benzyl)-1-((3-methylbutanoyloxy)methyl)piperazin-1-ium iodide;

1-((isopropylcarbamoyloxy)methyl)-1-methyl-4-(4-(4-methyl-3-(4-(pyridin-3-yl)pyrimidin-2-ylamino)phenylcarbamoyl)benzyl)piperazin-1-ium iodide;

(R)-1-methyl-4-(4-(4-methyl-3-(4-(pyridin-3-yl)pyrimidin-2-ylamino)phenylcarbamoyl)benzyl)-1-(((1-phenylethoxy)carbonyloxy)methyl)piperazin-1-ium iodide;

(R)-1-methyl-4-(4-(4-methyl-3-(4-(pyridin-3-yl)pyrimidin-2-ylamino)phenylcarbamoyl)benzyl)-1-((1-phenylethylcarbamoyloxy)methyl)piperazin-1-ium iodide;

(R)-1-((sec-butoxycarbonyloxy)methyl)-1-methyl-4-(4-(4-methyl-3-(4-(pyridin-3-yl)pyrimidin-2-ylamino)phenylcarbamoyl)benzyl)piperazin-1-ium iodide;

1-methyl-4-(4-(4-methyl-3-(4-(1-((sec-butoxycarbonyloxy)methyl)-pyridinium-3-yl)pyrimidin-2-ylamino)phenylcarbamoyl)benzyl)piperazine iodide;

1-(isobutyryloxymethyl)-1-methyl-4-(4-(4-methyl-3-(4-(pyridin-3-yl)pyrimidin-2-ylamino)phenylcarbamoyl)benzyl)piperazin-1-ium iodide;

1-((benzyloxycarbonyloxy)methyl)-1-methyl-4-(4-(4-methyl-3-(4-(pyridin-3-yl)pyrimidin-2-ylamino)phenylcarbamoyl)benzyl)piperazin-1-ium iodide;

(R)-1-methyl-4-(4-(4-methyl-3-(4-(pyridin-3-yl)pyrimidin-2-ylamino)phenylcarbamoyl)benzyl)-1-(((1-phenylethoxy)carbonyloxy)methyl)piperazin-1-ium iodide;

1-methyl-4-(4-(4-methyl-3-(4-(pyridin-3-yl)pyrimidin-2-ylamino)phenylcarbamoyl)benzyl)-1-(((3-methylbutan-2-yloxy)carbonyloxy)methyl)piperazin-1-ium iodide;

1-((benzyl(methyl)carbamoyloxy)methyl)-1-methyl-4-(4-(4-methyl-3-(4-(pyridin-3-yl)pyrimidin-2-ylamino)phenylcarbamoyl)benzyl)piperazin-1-ium iodide;

(S)-1-methyl-4-(4-(4-methyl-3-(4-(pyridin-3-yl)pyrimidin-2-ylamino)phenylcarbamoyl)benzyl)-1-((1-phenylethylcarbamoyloxy)methyl)piperazin-1-ium iodide;

1-((ethoxycarbonyloxy)methyl)-1-methyl-4-(4-(4-methyl-3-(4-(pyridin-3-yl)pyrimidin-2-ylamino)phenylcarbamoyl)benzyl)piperazin-1-ium iodide;

1-((cyclobutoxycarbonyloxy)methyl)-1-methyl-4-(4-(3-methyl-4-(4-(pyridin-3-yl)pyrimidin-2-ylamino)phenylcarbamoyl)benzyl)piperazin-1-ium iodide;

1-methyl-4-(4-((4-methyl-3-((4-(pyridin-3-yl)pyrimidin-2-yl)amino)phenyl)carbamoyl)benzyl)piperazin-1-ium methanesulfonate;

1-((2,2-dimethylbutanoyloxy)methyl)-1-methyl-4-(4-(4-methyl-3-(4-(pyridin-3-yl)pyrimidin-2-ylamino)phenylcarbamoyl)benzyl)piperazin-1-ium iodide;

1-methyl-4-(4-(4-methyl-3-(4-(pyridin-3-yl)pyrimidin-2-ylamino)phenylcarbamoyl)benzyl)-1-((tert-pentyloxycarbonyloxy)methyl)piperazin-1-ium iodide;

1-methyl-4-(4-(4-methyl-3-(4-(pyridin-3-yl)pyrimidin-2-ylamino)phenylcarbamoyl)benzyl)-1-((2-phenylacetoxy)methyl)piperazin-1-ium iodide;

4-(4-((3-((4-(1-(((isopropoxycarbonyl)oxy)methyl)pyridin-1-ium-3-yl)pyrimidin-2-yl)amino)-4-methylphenyl)carbamoyl)benzyl)-1-methylpiperazin-1-ium monoiodide monomesylate; or 3-(2-((2-methyl-5-(4-((4-methylpiperazin-1-yl) methyl)benzamido)phenyl)amino)pyrimidin-4-yl)-1-(((morpholine-4-carbonyl)oxy)methyl)pyridin-1-ium monoiodide monomesylate.

20. The method of claim 1, wherein the subject is suffering from a tumoral disease.

* * * * *

UNITED STATES PATENT AND TRADEMARK OFFICE
CERTIFICATE OF CORRECTION

PATENT NO. : 9,907,796 B2
APPLICATION NO. : 15/266802
DATED : March 6, 2018
INVENTOR(S) : Rhushikesh Chandrabhan Deokar et al.

It is certified that error appears in the above-identified patent and that said Letters Patent is hereby corrected as shown below:

In the Claims

In Claim 15, Column 82, Line 11, "chloromethyl 2-methoxy ethyl carbonate" should read as --chloromethyl 2-methoxyethyl carbonate--.

Signed and Sealed this
Fifteenth Day of May, 2018

Andrei Iancu
*Director of the United States Patent and Trademark Office*